United States Patent
Matts et al.

(10) Patent No.: US 12,188,815 B2
(45) Date of Patent: Jan. 7, 2025

(54) ULTRAVIOLET IMAGING SYSTEMS AND METHODS

(71) Applicant: The Procter & Gamble Company, Cincinnati, OH (US)

(72) Inventors: Paul Jonathan Matts, Addlestone (GB); Jonathan Mark Crowther, Egham (GB)

(73) Assignee: The Procter & Gamble Company, Cincinnati, OH (US)

( * ) Notice: Subject to any disclaimer, the term of this patent is extended or adjusted under 35 U.S.C. 154(b) by 408 days.

(21) Appl. No.: 17/714,432

(22) Filed: Apr. 6, 2022

(65) Prior Publication Data

US 2022/0326074 A1    Oct. 13, 2022

Related U.S. Application Data

(60) Provisional application No. 63/171,603, filed on Apr. 7, 2021.

(51) Int. Cl.
*G01J 1/42*    (2006.01)
*A61B 5/00*    (2006.01)
(Continued)

(52) U.S. Cl.
CPC ............ *G01J 1/429* (2013.01); *A61B 5/0077* (2013.01); *A61B 5/441* (2013.01); *A61Q 17/04* (2013.01);
(Continued)

(58) Field of Classification Search
CPC .............................. A61B 5/441; A61B 5/0077
See application file for complete search history.

(56) References Cited

U.S. PATENT DOCUMENTS

| 4,749,865 A | 6/1988 | Scheller |
| 5,636,637 A | 6/1997 | Guiolet et al. |

(Continued)

FOREIGN PATENT DOCUMENTS

| CN | 103592252 A | 2/2014 |
| CN | 104359840 A | 2/2015 |

(Continued)

OTHER PUBLICATIONS

PCT Search Report and Written Opinion for PCT/US2022/023393 dated Jul. 6, 2022, 15 pages.

(Continued)

*Primary Examiner* — Dani Fox
(74) *Attorney, Agent, or Firm* — Alexandra S. Anoff

(57) ABSTRACT

Ultraviolet systems and methods are described for capturing images depicting absorption or remittance of ultraviolet radiation (UVR). An example system includes a camera comprising a monochrome camera sensor that is configured to capture images, a radiation source that is configured to output a UVR waveband, a filter component that is configured to differentiate at least one of a UVA waveband and a UVB waveband of the UVR waveband, and a polarizer component that is configured to cross polarize each of the UVA waveband and the UVB waveband. Further, the camera is configured to capture an image depicting an UVA amount of UVA absorption or remittance as projected on a surface area and an UVB amount of UVB absorption or remittance as projected on the surface area.

22 Claims, 6 Drawing Sheets

(51) Int. Cl.
*A61Q 17/04* (2006.01)
*G06T 7/00* (2017.01)
(52) U.S. Cl.
CPC .. *G06T 7/0012* (2013.01); *G06T 2207/30088* (2013.01)

(56) References Cited

U.S. PATENT DOCUMENTS

| | | | |
|---|---|---|---|
| 6,130,435 | A | 10/2000 | Rocklin |
| 6,907,193 | B2 | 6/2005 | Kollias et al. |
| 6,922,523 | B2 | 7/2005 | Merola et al. |
| 7,061,617 | B2 | 6/2006 | Querleux et al. |
| 7,376,346 | B2 | 5/2008 | Merola et al. |
| 7,937,227 | B2 | 5/2011 | Miura et al. |
| 8,598,535 | B2 | 12/2013 | Miura et al. |
| 9,662,061 | B2 | 5/2017 | De Guia et al. |
| 9,816,857 | B2 | 11/2017 | Rastegar et al. |
| 10,732,100 | B2 | 8/2020 | Haddad et al. |
| 2003/0157039 | A1 | 8/2003 | Ferrero et al. |
| 2004/0031927 | A1 | 2/2004 | Tsai et al. |
| 2004/0125996 | A1 | 7/2004 | Eddowes |
| 2004/0146290 | A1 | 7/2004 | Kollias et al. |
| 2004/0219684 | A1 | 11/2004 | Dueva-koganov et al. |
| 2006/0082764 | A1* | 4/2006 | Sottery ........... G01N 21/274 356/402 |
| 2006/0246019 | A1 | 11/2006 | Cole et al. |
| 2008/0224059 | A1 | 9/2008 | Ferrero et al. |
| 2010/0012850 | A1 | 1/2010 | Miura et al. |
| 2010/0014069 | A1 | 1/2010 | Miura et al. |
| 2010/0075360 | A1 | 3/2010 | Majeed et al. |
| 2010/0247443 | A1 | 9/2010 | Iwaki et al. |
| 2011/0092844 | A1 | 4/2011 | Seo et al. |
| 2012/0022472 | A1 | 1/2012 | Miura et al. |
| 2013/0300850 | A1* | 11/2013 | Millikan ........... G01J 3/0229 348/77 |
| 2014/0063504 | A1 | 3/2014 | Stanfield et al. |
| 2015/0108360 | A1 | 4/2015 | Stanfield et al. |
| 2016/0025481 | A1 | 1/2016 | Stanfield et al. |
| 2018/0113121 | A1 | 4/2018 | Kim et al. |
| 2018/0313694 | A1 | 11/2018 | Hu et al. |
| 2018/0321139 | A1 | 11/2018 | Helfmann et al. |
| 2019/0242745 | A1 | 8/2019 | Jung et al. |
| 2019/0292340 | A1 | 9/2019 | Jiang et al. |

FOREIGN PATENT DOCUMENTS

| | | |
|---|---|---|
| CN | 106645143 A | 5/2017 |
| CN | 106959285 A | 7/2017 |
| CN | 107064038 A | 8/2017 |
| CN | 206862889 U | 1/2018 |
| CN | 108760685 A | 11/2018 |
| CN | 108956606 A | 12/2018 |
| CN | 109632584 A | 4/2019 |
| DE | 202013004905 U1 | 12/2013 |
| EP | 0301042 A1 | 2/1989 |
| EP | 2389573 A2 | 11/2011 |
| EP | 3261519 A1 | 1/2018 |
| EP | 3445455 A1 | 2/2019 |
| EP | 3449240 A2 | 3/2019 |
| FR | 2587117 A1 | 3/1987 |
| FR | 2710151 A1 | 3/1995 |
| JP | H05248944 A | 9/1993 |
| JP | H05248945 A | 9/1993 |
| JP | 2002116197 A | 4/2002 |
| JP | 2005321333 A | 11/2005 |
| JP | 2011051859 A | 3/2011 |
| JP | 2011080915 A | 4/2011 |
| JP | 2012063180 A | 3/2012 |
| JP | 2014071007 A | 4/2014 |
| JP | 2014081294 A | 5/2014 |
| JP | 2017146211 A | 8/2017 |
| JP | 2020091297 A | 6/2020 |
| KR | 101763147 B1 | 8/2017 |
| KR | 20200058798 A | 5/2020 |
| TW | 201326736 A | 7/2013 |
| WO | 2006058306 A2 | 6/2006 |
| WO | 2014204007 A1 | 12/2014 |
| WO | 2017007083 A1 | 1/2017 |
| WO | 2017189923 A2 | 11/2017 |
| WO | 2019021205 A1 | 1/2019 |
| WO | 2019045386 A1 | 3/2019 |
| WO | 2019151374 A1 | 8/2019 |
| WO | 2019227601 A1 | 12/2019 |
| WO | 2020148454 A1 | 7/2020 |
| WO | 2020232047 A1 | 11/2020 |

OTHER PUBLICATIONS

Alexa Teichmann et al. "Investigation of the homogeneity of the distribution of sunscreen formulations on the human a href= "skin:characterization" target="_blank" skin: characterization/a and comparison of two different methods" vol. 11 (6), Dec. 28, 2006, pp. 064005-1 to 064005-8.

Anonymous: "Apochromat", Wikipedia, dated Jul. 23, 2020 (Jul. 23, 2020), XP055935037, Retrieved from the Internet:brURL Link :a href="https://en.wikipedia.org/wiki/Apochrom" target="_blank" https://en.wikipedia.org/wiki/Apochrom/a at [retrieved on Jun. 23, 2022]the whole document, 3 pgs.

Dr. Jürgen Lademann et al. "Influence of Microparticles on thebrHomogeneity of Distribution of Topically Applied Substances" Jul. 28, 2008, pp. 274-282.

Honda Y et al., "Structure and Performance of Cosmetic Powder on Skin Afterapplication", Oct. 24-27, 2004, 3 pages.

Ikehira M, Banno T et al. "Quantitative Analysis on the Influence of Spatial Inhomogeneity of UV Absorbers in the Applied Layer of Emulsion Type Sunscreen on In Vitro UV Protection Abilities", Sep. 18 -21, 2018, pp. 1-8.

J. M. Crowther, "Understanding sunscreen SPF performance using cross-polarized UVA reflectance photography" vol. 40, Dec. 11, 2017, pp. 127-133.

J. M. Crowther, "UV reflectance photography of skin: what are you imaging?", vol. 42, Nov. 12, 2019, pp. 136-145.

J. M. Crowther, "Calibrating UVA reflectance photographs—brstandardization using a low-cost method", vol. 41, Jul. 22, 2018, pp. 109-117.

Ken Nishino et al. "Development of the multispectral UV polarization reflectance imaging system (MUPRIS) for in situ monitoring of the UV protection efficacy of sunscreen on human skin" Feb. 16, 2019, pp. 639-652.

Peter W. Grencis et al. "An evaluation of photographic methods to demonstrate the uniformitythe skin", vol. 22, Jul. 10, 2009, pp. 171-177.

* cited by examiner

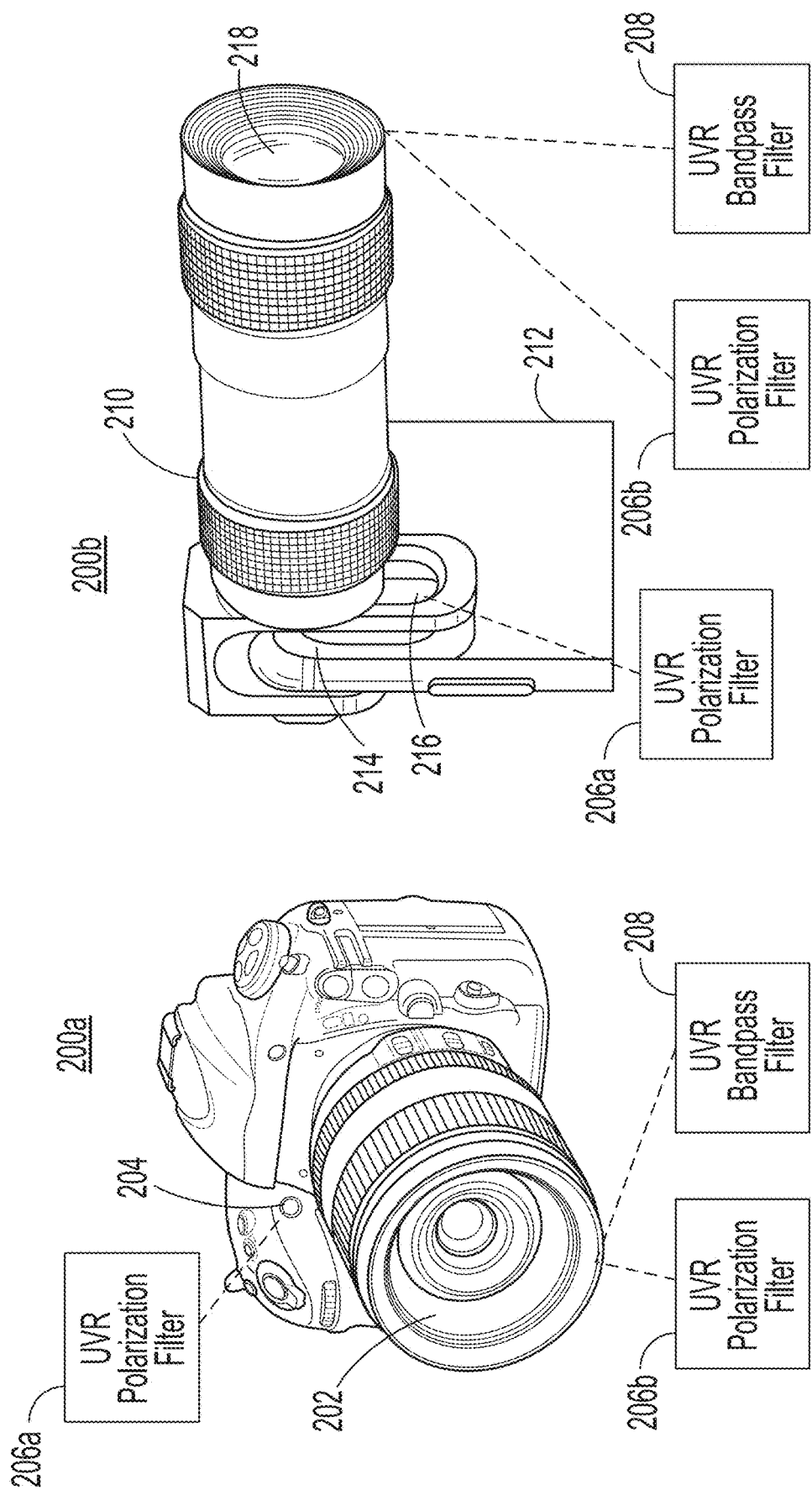

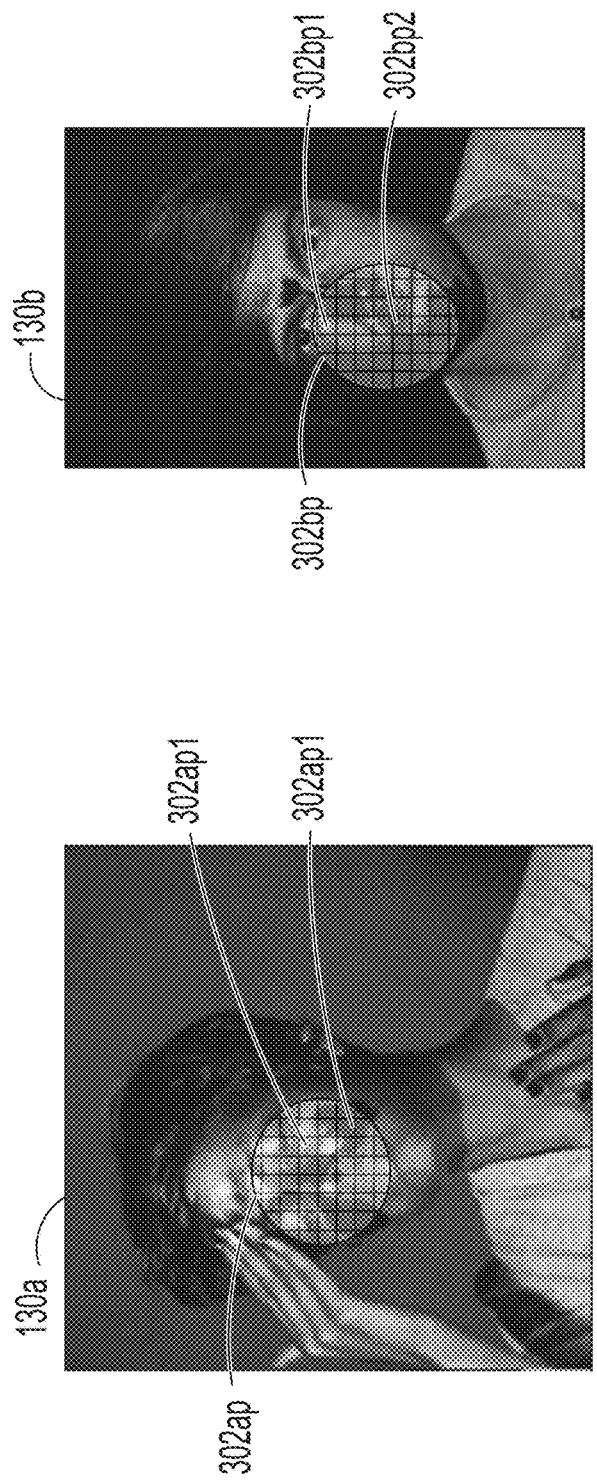
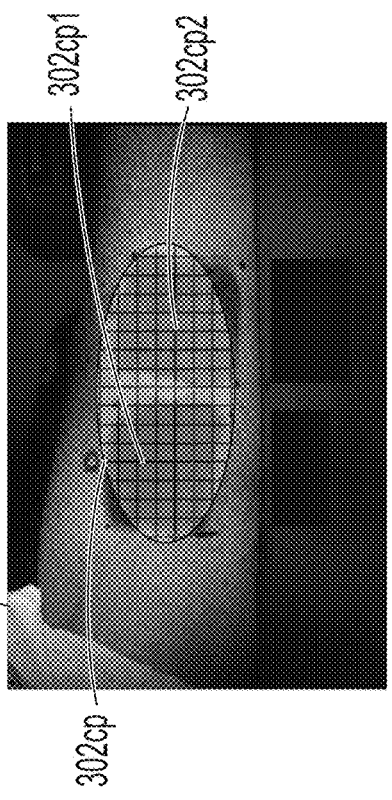
Fig. 2A  Fig. 2B  Fig. 2C

ULTRAVIOLET IMAGING SYSTEMS AND METHODS

FIELD

The present disclosure generally relates to ultraviolet imaging systems and methods, and more particularly to, ultraviolet imaging systems and methods configured to capture images depicting absorption or remittance of ultraviolet radiation (UVR).

BACKGROUND

Generally speaking, billions of people are exposed to UVR from the sun on a daily basis, and an increasing number of people are exposed to artificial sources used in recreation, industry, and commerce. The human skin is very susceptible to damage resulting from exposure to UVR, but proper application of a sunscreen with an appropriate sun protection factor (SPF) can mitigate these effects. Problematically, many people do not regularly apply sunscreen to areas of their skin that are frequently exposed to UVR. And, when a person does apply sunscreen, it can be difficult to see whether the sunscreen product has been applied adequately because most conventional sunscreen products are clear. Digital methods of evaluating whether a person has adequately applied a sunscreen product (e.g., using an "app" in conjunction with a smart phone camera or the like) also may not provide a suitable indication of adequate sunscreen application due to poor image quality resulting from, for example, specular reflection.

As a result, many people may neglect evaluating the efficacy of their sunscreen application, and may neglect applying sunscreen altogether from a general lack of understanding. The problem is acutely pronounced given the myriad of skin conditions that may develop as a result of neglecting proper sunscreen application, and the associated myriad of sunscreen products available. Such existing sunscreen products may also provide little or no feedback or guidance to assist the user in determining how best to utilize the product with their skin. Thus, many people may incorrectly apply the sunscreen product because they are unaware of proper application techniques and how much sunscreen is required for adequate protection.

Accordingly, there is a need for an improved UVR imaging system that can capture images of absorption and/or remittance of UVR, thereby enabling a user to determine if they have adequately applied a sunscreen product.

SUMMARY

Disclosed herein is an ultraviolet radiation (UVR) imaging system configured to capture images depicting absorption or remittance of UVR, the UVR imaging system comprising: a camera comprising a monochrome camera sensor; a radiation source configured to output a UVR waveband; a filter component configured to differentiate at least one of a UVA waveband and a UVB waveband of the UVR waveband; and a polarizer component configured to cross polarize each of the UVA waveband and the UVB waveband, wherein the camera is configured to capture an image depicting an UVA amount of UVA absorption or remittance as projected on a surface area and an UVB amount of UVB absorption or remittance as projected on the surface area. Methods of using the UVR imaging system are also described herein.

BRIEF DESCRIPTION OF THE DRAWINGS

FIGS. 1A and 1B illustrate examples of a UVR imaging system.

FIGS. 2A, 2B and 2C illustrate example images and related pixel data.

DETAILED DESCRIPTION OF THE INVENTION

Figure 3:
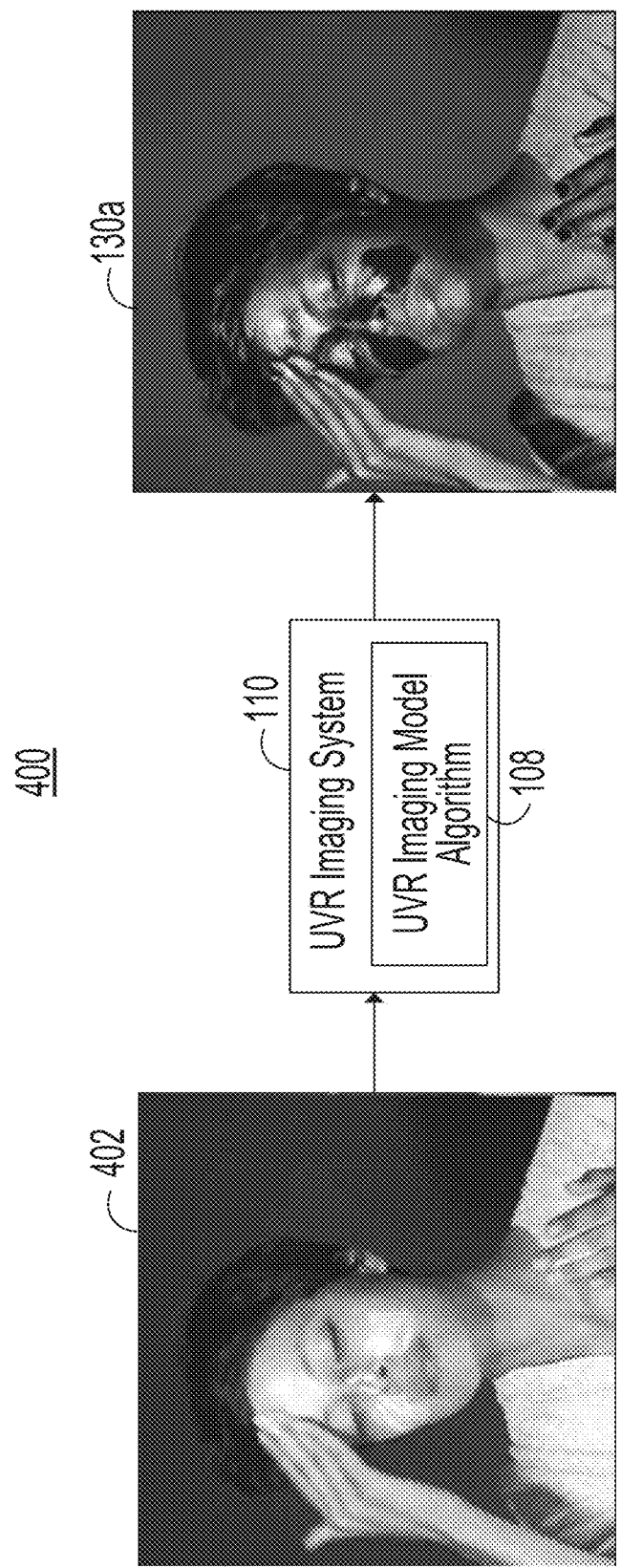
FIG. 3 is an example flow diagram of the UVR imaging systems of FIGS. 1A and 1B.

The imaging system and methods herein introduce improvements to the fields of UVR imaging systems and skin care. For example, the UVR imaging systems of the present disclosure enable a user to quickly and conveniently capture images (e.g., images of a user's face or target skin surface) and receive an indication of areas where a product (e.g., a sunscreen product) has been applied and/or areas where further application of the product may be needed. For example, an indication of product application can be provided on a display of a user's mobile device. The trained UVR imaging model algorithm of the present UVR imaging system improves the field of UVR imaging systems with digital and/or artificial intelligence based analysis of user-specific images to output an output to address user-specific pixel data included in the captured images of the surface (e.g., a user's skin surface).

The present UVR imaging system provides several specific improvements over conventional UVR imaging systems. For example, conventional UVR imaging systems suffer from low resolution images that do not allow analysis of product film morphology applied on a surface. An example image captured by a conventional UVR imaging system may feature, for example, a resolution of approximately 680 pixels by approximately 512 pixels. As a result, the images captured by conventional UVR imaging systems may only provide an "average UV absorbance" of the imaged surface, without an indication of how well the product forms a film on the target skin surface (e.g., morphology). By contrast, the present UVR imaging systems and methods utilize a camera that provides high resolution images of a surface, thereby allowing effective product film morphology analysis. The most preferable sensor size of the camera used in the UVR imaging systems of the present disclosure is greater than 25 megapixels with a preferable sensor size of greater than 10 megapixels. Thus, the UVR imaging systems of the present disclosure capture images with approximately one-hundred times greater resolution than conventional UVR imaging systems. Accordingly, the UVR imaging systems of the present disclosure enable effective imaging and analysis of product film morphologies across UVR wavebands that was previously unattainable with conventional UVR imaging systems/techniques. Specifically, the UVR imaging systems and methods of the present disclosure achieve a 10-fold increase in the resolution of objects imaged compared to conventional UVR imaging systems. For example, the UVR imaging systems and methods enable fine detail imaging of product film morphologies applied to a skin surface, as measured by, for example, the Modulation Transfer Function (a means of evaluating the fundamental spatial resolution performance of an imaging system), which is known to those skilled in the art of imaging systems.

As another example, images captured by conventional UVR imaging systems generally suffer from a lack of focus. Namely, conventional UVR imaging systems suffer from a lack of apochromaticity, and therefore can only achieve sufficient focus in a small number of wavelengths for a particular image capture. As a result, images captured by conventional UVR imaging systems feature chromatic aberrations and spherical aberrations resulting from a lack of focus at multiple wavelengths. By contrast, the UVR imaging systems and methods of the present disclosure may include an apochromatic lens that reduces/eliminates chromatic aberrations and spherical aberrations from the captured images. Accordingly, the apochromatic lens provides sufficient focus at multiple wavelengths (e.g., UVA and UVB) in a single image that was previously unattainable with conventional UVR imaging systems/techniques. The apochromatic lens of the present disclosure can image all required UVR wavelengths without the need to re-focus at each UVR wavelength, unlike conventional UVR imaging systems. As a result, the UVR imaging systems and methods of the present disclosure provide a significantly faster capture process that minimizes potential error by eliminating the need to apply and adjust/focus multiple lenses between image captures.

As yet another example, conventional UVR imaging systems suffer from a lack of brightness calibration. Without calibration, it is impossible to quantify the amount of UVR absorbance/remittance in the acquired image, allowing only relative comparisons. By contrast, the UVR imaging systems and methods of the present disclosure provide a calibration standard for the image capture process, to ensure that each image is captured under comparable illumination. As a result, the calibration standard allows absolute determinations of UVR absorbance/remittance by an imaged surface (e.g., human skin, a product film), thereby enabling the quantification of, for example, skin components and/or sunscreen concentration that was previously unachievable with conventional UVR imaging systems.

As still another example, conventional UVR imaging systems suffer from utilizing radiation sources that provide a variety of unwanted wavelengths of radiation. To compensate, conventional UVR imaging systems typically include a filter wheel disposed in front of the radiation source to remove the unwanted wavelengths. By contrast, the UVR imaging systems and methods of the present disclosure include a radiation source that emits intense UVA and UVB radiation at particular wavelengths of interest (e.g., 313 nm and 365 nm). The radiation source of the present disclosure thereby eliminates the need for additional filters present in conventional UVR imaging systems/techniques. Further, certain aspects of the UVR imaging systems and methods of the present disclosure include continuously emitting UVR radiation sources (e.g., xenon bulbs, mercury xenon bulbs) that continuously emit UVR during a tunable image capture period of the UVR imaging system. As a result, the continuously emitting UVR radiation sources of the present disclosure allow for increased exposure times and correspondingly enable higher quality image captures over conventional UVR imaging systems/techniques that are reliant on conventional UVR radiation sources.

As yet another example, conventional UVR imaging systems generally suffer from over-exposure, that is, where the signal to the camera sensor exceeds the dynamic range of response, resulting in a significant loss of image information. Typically, this over-exposure is the result of inefficient polarization in the UVR wavelengths of interest, which produces specular reflection (or "shine") in captured images. Specular reflection is an unwanted artefact caused by photons remitted from the surface of the imaged substrate (e.g., skin surface, product, or another material), meaning that no information is returned to the camera sensor related to scattering or absorption within the imaged substrates. As a result, specular reflection makes it impossible to understand or quantify skin or sunscreen components in the imaged field of view (FOV). By contrast, the UVR imaging systems and methods herein include UVR polarizing filters that are configured to eliminate specular reflection in images captured using a UVR illumination source that are otherwise present when using conventional UVR imaging systems/techniques. Thus, the UVR imaging systems and methods of the present disclosure are able to accurately and consistently identify and quantify skin or sunscreen components in the imaged FOV in a manner previously unachievable with conventional UVR imaging systems.

As still another example, conventional UVR imaging systems generally suffer from a lack of sensitivity in discriminating between specific UVR wavebands because, for example, a typical radiation source is incapable of emitting wavelengths within these UVR wavebands and filters are typically not used to isolate specific UVR wavebands. By contrast, the UVR imaging systems and methods herein include a radiation source that emits radiation across the terrestrial UVR spectrum (290-400 nm), any may specifically emit wavelengths within specified wavebands of interest (e.g., UVA and UVB wavebands), thereby providing increased UVR sensitivity over conventional UVR imaging systems. Moreover, the UVR imaging systems and methods of the present disclosure also include narrow bandpass filters that isolate specific regions of the terrestrial UVR spectrum (for example, narrow wavebands centered in the UVB and UVA wavebands) to further increase UVR sensitivity over conventional UVR imaging systems.

In addition, the present disclosure includes specific features other than what is well-understood, routine, conventional activity in the field, or adding unconventional steps that confine the claim to a particular useful application, e.g., capturing images for analysis using a UVR imaging system configured to capture images of a surface depicting an UVA amount of UVA absorption or remittance as projected on the surface and an UVB amount of UVB absorption or remittance and projected on the surface.

For similar reasons, the present disclosure includes improvements in computer functionality or in improvements to other technologies at least because the disclosure describes that, e.g., a user computing device, an imaging server, or other computing device, is improved where the intelligence or predictive ability of the user computing device, the imaging server, or other computing device is enhanced by a trained UVR imaging model algorithm. The UVR imaging model algorithm, executing on the user computing device or imaging server, is able to accurately determine, based on pixel data of the imaged surface, one or more attributes of application of a product to the surface. In various aspects, the UVR imaging model algorithm may also generate an output (e.g., for a manufactured product, application techniques, medical attention, etc.) designed to address the one or more attributes of application identifiable within the pixel data of the imaged surface.

That is, the present disclosure describes improvements in the functioning of the computer itself or "any other technology or technical field" because a user computing device or imaging server, is enhanced with a plurality of training images (e.g., 10,000s of training images and related pixel data) to accurately determine one or more attributes of application of a product, and to accurately detect, identify, and/or otherwise analyze pixel data of a user-specific image(s), such as newly provided user images. This improves over the prior art at least because existing systems lack such real-time generative or classification functionality and are simply not capable of accurately analyzing user-specific images to output a user-specific result to address one or more attributes of application identifiable within the pixel data of the imaged surface.

FIG. 1A illustrates an example UVR imaging system 200a configured to capture images depicting absorption or remittance of UVR, in accordance with various aspects disclosed herein. The example UVR imaging system 200a in FIG. 1A includes a digital camera configured to capture monochrome images depicting absorption or remittance of UVR. For example, the camera may be a stock camera that is converted to capture monochrome images by removing the color filter.

The UVR imaging system 200a is easy to use, portable, and may capture images with high resolution and enhanced UVR (and particularly UVB) sensitivity. The high resolution images may allow the example UVR imaging system 200a (e.g., via the UVR imaging model algorithm 108) to, for example, analyze and display streaks and/or other surface aberrations contained in the application of a sunscreen film to a skin surface, and thereby determine the effectiveness/quality of the sunscreen film on the skin surface. Additionally or alternatively, the example UVR imaging system 200a may be a machine vision camera configured to implement one or more machine vision tasks when performing one or more of the actions described herein.

The UVR imaging system 200a illustrated in FIG. 1A includes a lens 202, which may be configured to focus UVR for the UVR imaging system 200a during image capture. In some aspects, the lens 202 may be an apochromatic lens. For example, the lens 202 may be configured to focus UVR at wavelengths of approximately 313 nanometers (nm) and approximately 365 nm, without refocusing the UVR imaging system 200a, to provide sharp, focused images at the UVR wavelengths of interest. Of course, it will be appreciated that the lens 202 may be configured to focus UVR of any suitable wavelength(s) of interest.

The UVR imaging system 200a includes a radiation source 204. Generally, the radiation source 204 may be configured to output radiation in a UVR waveband. For example, the radiation source 204 may output radiation in a wavelength range including 290 nm to 400 nm. In some aspects, the radiation source 204 may be discontinuous, with an output peak of between about 290 nm and 400 nm, and may include intense, discreet bands of UVR at approximately 313 nm (e.g., approximately at the center of the UVB radiation waveband) and approximately 365 nm (e.g., approximately at the center of the UVA radiation waveband). The radiation source 204 may also be a continuous radiation source (that is, without intense, discreet bands of UVR) and may have an output diameter sufficient to allow the use of small diameter polarizers/filters (e.g., less than approximately 50 mm in diameter). For example, the radiation source 204 may be any one of one or more xenon bulbs, one or more mercury xenon bulbs, one or more light emitting diode (LED) sources, and/or any other suitable UVR radiation source or combinations thereof. Of course, it will be appreciated that the radiation source 204 may be a flash radiation source, and may output radiation in any suitable UV wavelength range, including for example, any wavelengths in the UVA, the UVB, and/or the UVC wavebands. Moreover, it will be appreciated that, in certain aspects, the radiation source 204 may be a non-integrated component (e.g., physically separate/distinct) of the camera represented in the UVR imaging system 200a. For example, in these aspects, the radiation source 204 may be a standalone mercury lamp that is configured to produce UVR of particular wavelengths of interest (e.g., within the UVA and UVB wavebands) in connection with an image capture of the stock camera represented in the UVR imaging system 200a.

The UVR imaging system 200a illustrated in FIGS. 1A and 1B includes two UVR polarizing filters 206a, 206b that cross-polarize UVR from the radiation source 204, thereby reducing the specular reflection in captured images. The UVR polarizing filter 206a may be disposed between the radiation source 204 and the surface to be imaged, and the UVR polarization filter 206b may be detachably coupled to the UVR imaging system 200a by attaching the filter 206b to the front of the lens 202. In certain aspects, the UVR polarizing filter 206a may be removably or permanently attached to the radiation source 204. In order to cross-polarize the UVR emitted by the radiation source 204, the UVR polarization filter 206b may be rotated approximately ninety degrees with respect to the UVR polarization filter 206a.

In some aspects, the UVR polarizing filters 206a, 206b may polarize radiation of the UVR waveband having a wavelength of between 220 nm and 400 nm. For example, the UVR polarizing filters 206, 206b may be configured to polarize UVR having a wavelength of approximately 313 nm and approximately 365 nm to increase the imaging sensitivity in the UVB and UVA wavebands. In some aspects, the UVR polarizing filters 206a, 206b may have a diameter of between about 5 mm and about 50 mm. Of course, it is to be understood that the UVR polarizing filters 206a, 206b may have any suitable diameter. For example, if the radiation source 204 is a studio flash source, then the UVR polarizers 206a, 206b may have a diameter of 200 mm or greater. Additionally or alternatively, if the radiation source 204 is a LED, then the UVR polarizers 206a, 206b may have a diameter of 5 mm or less.

The UVR imaging system 200a may also include a UVR bandpass filter 208. Generally, the UVR bandpass filter 208 may be detachably coupled to the example UVR imaging system 200a by attaching the filter 208 to the front of the lens 202. The UVR bandpass filter 208 may generally transmit UVR of a narrow range of wavelengths, thereby minimizing chromatic aberrations within captured images. As a result, the UVR bandpass filter 208 may increase the focus of the captured images by isolating and differentiating regions of the UVR wavebands of interest (e.g., UVA and UVB).

In general, the UVR bandpass filter 208 may be any suitable filter configured to filter UVR wavebands. For example, in some aspects, the UVR bandpass filter 208 may be and/or include a dichroic coated filter, which may provide a high degree of filtration corresponding to wavelengths outside of UVR wavebands. In some aspects, the UVR bandpass filter 208 may include multiple UVR bandpass filters. The multiple UVR bandpass filters may include, for example, a 313 nm narrow bandpass filter with a 10 nm full width half maximum (FWHM) and a 365 nm narrow bandpass filter with a 10 nm FWHM. In this example, the 313 nm narrow bandpass filer with a 10 nm FWHM will differentiate fully and exclusively, for example, the UVB bandwidth (290-320 nm; with the FWHM range spanning 308-318 nm) and the 365 nm narrow bandpass filter with a 10 nm FWHM will differentiate fully and exclusively, for example, the UVA bandwidth (320-400 nm; with the FWHM range spanning 360-370 nm). In this manner, the UVR bandpass filter 208 may substantially increase the UVR sensitivity of the UVR imaging systems and methods of the present disclosure over conventional UVR imaging systems. In some aspects, the UVR bandpass filter 208 may be configured to filter at least a portion of other radiation of the UVR waveband, as depicted in the captured image. Of course, it is to be understood that bandpass filters configured to filter any suitable wavelength(s) within the UVR wavebands may be used.

FIG. 1B illustrates another example of a UVR imaging system 200b that includes a UVR imaging attachment 210 detachably or permanently coupled to a mobile device 212 such as a smart phone or tablet. The UVR imaging attachment 210 may generally include imaging components configured to transmit UVR wavebands of interest to, for example, a camera 214 of the mobile device 212 to capture an image of a surface illuminated by a UVR light source 216. The camera 214 and the UVR light source 216 may be integrated components of the mobile device 212, and the UVR light source 216 may be configured to emit UVR in the wavelength(s) of interest (e.g., UVA and UVB). It will be appreciated that the camera 214 and the UVR light source 216 may be additional external components that are attached to the mobile device 212 via any suitable connection (e.g., USB, BLUETOOTH, WiFi, etc.).

Further, the UVR imaging attachment 210 may include a lens 218, the UVR polarization filters 206a, 206b, and the UVR bandpass filter 208. The lens 218 may be configured to focus UVR for the example UVR imaging system 200b during image capture. The lens 218 may be an apochromatic lens, and/or any other suitable lens configured to provide sharp, focused images at the UVR wavelength(s) of interest. The UVR polarization filters 206a, 206b may be configured to cross-polarize the UVR emitted/received by/from the radiation source 204, thereby reducing the specular reflection in captured images. The UVR bandpass filter 208 may generally transmit UVR of a narrow range of wavelengths, thereby minimizing chromatic aberrations within captured images. Each of the lens 218, the UVR polarization filters 206a, 206b, and the UVR bandpass filter 208 may be detachably coupled to the mobile device 212 and/or each other. For example, the UVR polarization filter 206b and the UVR bandpass filter 208 may be detachably coupled to the UVR imaging attachment 210 by attaching the filters 206b, 208 to the front of the lens 218, and the UVR polarizing filter 206a may be detachably coupled to the UVR light source 216.

In some aspects, the example UVR imaging systems 200a, 200b may further include one or more digital processors, one or more digital memory storage devices communicatively coupled to the one or more processors, a digital imaging model, and computing instructions that are executable by the one or more processors, and stored on the one or more memories. As further discussed herein, the imaging model may be trained with a plurality of images (e.g., 100, 1,000, or even 10,000 or more images) each depicting a respective UVA amount of UVA absorption or remittance as projected on a respective surface area, and a respective UVB amount of UVB absorption or remittance as projected on the respective surface area. The imaging model may be trained, for example, to determine one or more respective attributes of application of a product (e.g., sunscreen).

Further in these aspects, the computing instructions may be executed by the one or more processors to cause the one or more processors to analyze a captured image with the imaging model to determine one or more attributes of application of the product. The surface area depicted in the image may include an area of a user's skin, and the one or more determined attributes may specific to the user's skin.

In some aspects, the example UVR imaging systems 200a, 200b, may further include a display screen that may be configured to receive/display an image captured by the example UVR imaging systems 200a, 200b. The display screen may be an integrated component of the example UVR imaging systems 200a, 200b (e.g., a display screen of the mobile device 212), and/or the display screen may be an external component that is connected to the example UVR imaging systems 200a, 200b through any suitable connection (e.g., USB, BLUETOOTH, WiFi, etc.). Moreover, the display screen may be configured to render the image captured by the example UVR imaging systems 200a, 200b in real-time or near real-time upon or after capture of the image by the example UVR imaging systems 200a, 200b. For example, the display screen may render the image in real-time as the image is captured, and/or within approximately one to two seconds after image capture.

In some aspects, the camera (e.g., camera 214), the radiation source (e.g., radiation source 204, UVR light source 216), the filter component (e.g., UVR bandpass filter 208), and/or the polarizer component (e.g., UVR polarization filter 206a, UVR polarization filter 206b) can be integral components of a UVR imaging device. In these aspects, the UV imaging device may be configured for attachment to or integration with a mobile device (e.g., mobile device 212). Further in these aspects, the UVR imaging device may include a mobile application (app) configured to operate on the mobile device and may be communicatively coupled to the UVR imaging device. The mobile app may include computing instructions executable by one or more processors of the mobile device, and that may be stored on a non-transitory computer-readable medium of the mobile device. The computing instructions, when executed by the one or more processors, may cause the one or more processors to render, on a display screen of the mobile device, the image, and may further render an output textually describing or graphically illustrating the UVA amount or the UVB amount, as depicted in the image. Moreover, the computing instructions, when executed by the one or more processors, may cause the one or more processors to render, on the display screen of the mobile device, an output informing a user of at least one of an application quality of a product (e.g., sunscreen) to the user's skin, or an application of a quantity of the product to the user's skin.

FIGS. 2A, 2B and 2C illustrate example images 130a, 130b, and 130c captured by, for example, UVR imaging systems 200a, 200b to determine attribute(s) of application of a product applied to an imaged surface (e.g., a user's skin). Each of these images 130a, 130b and 130c may be analyzed by, and/or used to train, a UVR imaging model algorithm (e.g., UVR imaging model algorithm 108). In some aspects, the captured images may be aggregated at imaging server(s) 102 and may be analyzed by, and/or used to train, the UVR imaging model algorithm (e.g., an AI model such as a machine learning imaging model, as described herein).

Each example image 130a, 130b, 130c includes pixel data 302ap, 302bp, and 302cp (e.g., grayscale/monochrome data and/or RGB data) representing UVR data and corresponding to an UVA amount of UVA absorption or remittance as projected on a surface area and/or an UVB amount of UVB absorption or remittance as projected on the surface area. Generally, as described herein, the pixel data 302*ap*, 302*bp*, and 302*cp* includes points or squares of data within an image, where each point or square represents a single pixel (e.g., pixels 302*ap*1, 302*ap*2, 302*bp*1, 302*bp*2, 302*cp*1, and 302*cp*2) within an image. Each pixel may be a specific location within an image, and each pixel may have a specific color (or lack thereof). When color pixels are used, pixel color may be determined using a known color format (e.g., 24-bit RGB color format) and related channel data associated with a given pixel. Some non-limiting examples of color formats that may be used herein are described in U.S. Pat. Nos. 3,971,065 and 7,679,782.

The channel data representing the RGB color format components may be combined, for example, in post-processing by an imaging device (e.g., example UVR imaging systems 200*a*, 200*b*) to achieve a monochromatic value corresponding to each pixel. These monochromatic values may represent the perceived brightness/intensity of the illumination received by the imaging device that was reflected from the object/surface represented by the pixel in the image. Additionally or alternatively, the imaging device may be configured to capture monochromatic image data, which may be, for example, various shades of black representing the brightness/intensity of the illumination received by the imaging device that was reflected from the object/surface represented by the pixel in the image.

As a whole, the various pixels, positioned together in a grid pattern, form a digital image (e.g., images 130*a*, 130*b*, and/or 130*c*). A single digital image can include thousands or millions of pixels. Images can be captured, generated, stored, and/or transmitted in a number of formats, such as JPEG, TIFF, PNG and GIF. These formats use pixels to store and represent the image.

FIG. 2A illustrates an example of an image 130*a* and its related pixel data (e.g., pixel data 302*ap*) captured by a UVR imaging systems. The example image 130*a* is a monochromatic image depicting a user applying a product (e.g., sunscreen) to the user's facial skin. It may be desirable to configure the UVR imaging system such that a user can capture an image of any portion of the body where products (e.g., skin care products such as sunscreen) are applied, including, for example, the face, underarm, chest, back, leg, arm, hand, feet, and combinations thereof.

The example image 130*a* contains pixel data 302*ap* including, for example, pixels 302*ap*1 and 302*ap*2. Pixel 302*ap*1 may be a relatively light pixel (e.g., a pixel with high R, G, and B values and/or high grayscale/monochromatic values) positioned in the example image 130*a* resulting from the user having a relatively low degree of product application at the position represented by pixel 302*ap*1 due to, for example, improper product application technique or volume. Pixel 302*ap*2 may be a relatively darker pixel (e.g., a pixel with low R, G, and B values and/or low grayscale/monochromatic values) positioned in the example image 130*a* resulting from the user having a relatively high degree of product application at the position represented by pixel 302*ap*2.

UVR imaging systems 200*a*, 200*b* may be used to capture the example image 130*a* and analyze the characteristics represented by the pixel data (e.g., pixel data 302*ap*). For example, the example UVR imaging systems 200*a*, 200*b* may analyze the relatively light pixel represented by pixel 302*ap*1 and the relatively darker pixel represented by pixel 302*ap*2 and determine that the user has applied an insufficient amount of product (e.g., sunscreen) to the user's skin. Namely, and as discussed further herein, the example UVR imaging systems 200*a*, 200*b* may determine (e.g., via the UVR imaging model algorithm 108) that the color values of the pixels 302*ap*1, 302*ap*2 in combination with the position of the pixels 302*ap*1, 302*ap*2 relative to the recognized facial area of the user indicate that the user has not applied a sufficient amount of sunscreen product to the user's facial area to adequately protect the sensitive locations of the user's facial area from damaging UVR.

FIG. 2B illustrates a further example of an image 130*b* and its related pixel data 302*bp*. The example image 130*b* illustrates a user who has applied a product to a portion of their face. The example image 130*b* may represent, for example, the user attempting to determine the proper application of sunscreen to their face, as discussed herein.

Example image 130*b* contains pixel data 302*bp*, which includes a plurality of pixels (e.g., pixels 302*bp*1 and 302*bp*2). In this example, pixel 302*bp*1 is a relatively light pixel (e.g., a pixel with high R, G, and B values and/or high grayscale/monochromatic values) resulting from the user having a relatively low degree of product application at the position represented by pixel 302*bp*1. In this example, pixel 302*bp*2 is a relatively darker pixel (e.g., a pixel with low R, G, and B values and/or low grayscale/monochromatic values) positioned in the example image 130*b* resulting from the user having a relatively high degree of product application at the position represented by pixel 302*bp*2.

UVR imaging systems 200*a*, 200*b* may be used to capture the example image 130*b* and analyze the characteristics represented by the pixel data (e.g., pixel data 302*bp*). For example, the example UVR imaging systems 200*a*, 200*b* may analyze the relatively light pixel represented by pixel 302*bp*1 and the relatively darker pixel represented by pixel 302*bp*2 and determine that the user has misapplied a product (e.g., sunscreen) to the user's skin. Namely, and as discussed further herein, the example UVR imaging systems 200*a*, 200*b* may determine (e.g., via the UVR imaging model algorithm 108) that the color values of the pixels 302*bp*1, 302*bp*2 in combination with the position of the pixels 302*bp*1, 302*bp*2 relative to the recognized facial area of the user indicate that the user has not applied a sunscreen product appropriately (e.g., used correct sunscreen application technique) to the user's facial area to adequately protect the sensitive locations of the user's facial area from damaging UVR.

FIG. 2C illustrates a further example image 130*c* and its related pixel data (e.g., 302*cp*). The example image 130*c* depicts a user's forearm with multiple sunscreen products that have different UVA and UVB absorption/remittance characteristics applied thereto. As can be seen in FIG. 2C, the UVR imaging system enables a user to determine which sunscreen product has superior absorption/remittance characteristics in UVA and/or UVB, as discussed further herein.

The pixel data 302*cp* of image 130*c* includes a plurality of pixels including pixels 302*cp*1 and 302*cp*2. As an example, assume that the example UVR imaging systems 200*a*, 200*b* captured the example image 130*c* under illumination consisting primarily of UVB radiation (e.g., from radiation source 204). In this example, pixel 302*cp*1 is a relatively dark pixel and pixel 302*cp*2 is a relatively light pixel.

UVR imaging systems 200*a*, 200*b* may be used to capture the example image 130*c*, analyze the characteristics represented by the pixel data (e.g., pixel data 302*cp*), and/or provide a product recommendation as a result of the analysis. For example, the example UVR imaging systems 200*a*, 200*b* may analyze the relatively dark pixel represented by pixel 302cp1 and the relatively lighter pixel represented by pixel 302cp2 and determine that the product represented by the pixel 302cp1 has a superior UVB absorption characteristic when compared with the product represented by the pixel 302cp2. Namely, and as discussed further herein, the example UVR imaging systems 200a, 200b may determine (e.g., via the UVR imaging model algorithm 108) that the color values of the pixels 302cp1, 302cp2 in combination with a known wavelength(s) of illumination (e.g., radiation source 204 emitting UVB radiation) indicate that the user should apply the product represented by the pixel 302cp1 in order to better protect the user's skin against harmful UVB radiation.

The pixel data 302ap, 302bp, and 302cp each include various remaining pixels including remaining portions of the user's skin surface area featuring varying lightness/darkness values and color values. The pixel data 302ap, 302bp, and 302cp each further include pixels representing further features including the undulations of the user's skin due to anatomical features of the user's skin surface and other features as shown in FIGS. 2A, 2B and 2C.

It is to be understood that each of the images represented in FIGS. 2A, 2B and 2C may arrive and be processed in accordance with a UVR imaging model algorithm (e.g., UVR imaging model algorithm 108), as described further herein, in real-time and/or near real-time. For example, a user may capture the example image 130c immediately after application of both products to the user's skin, and the UVR imaging model algorithm may provide feedback, recommendations, and/or other comments in real-time or near real-time. However, in some aspects, the example UVR imaging systems 200a, 200b may capture each of the images represented in FIGS. 2A, 2B and 2C and display the raw images on a display screen for viewing by a user without additional processing (e.g., via the UVR imaging model algorithm 108) and/or feedback, recommendations, and/or other comments.

FIG. 3 illustrates an example flow diagram of a UVR imaging system 110 (e.g., UVR imaging systems 200a, 200b) capturing an input image 402 to generate the example image 130a depicting absorption or remittance of UVR as projected on the surface area of the imaged surface. Generally, and as previously mentioned, the UVR imaging system 110 captures the image 402 utilizing UVR imaging components (e.g., lens 202, radiation source 204, UVR polarization filter 206a, 206b, UVR bandpass filter 208), wherein the captured radiation indicated in the pixel data (e.g., pixel data 302ap) of the example image 130a indicates an amount of UVR reflectance/absorption associated with the surface area corresponding to the pixel data. In some aspects, the example image 130a may be displayed to a user (e.g., the user displayed in the example image 130a) to allow the user to view/determine how well the user applied a product to user's skin surface.

Additionally or alternatively, the UVR imaging system 110 may utilize the UVR imaging model algorithm 108 to analyze pixel values of the example image 130a to determine attributes of application of the product on the user's skin surface. For example, the UVR imaging system 110 may apply the UVR imaging model algorithm 108 to the example image 130a, and the UVR imaging model algorithm 108 may determine that the user has applied an insufficient amount of product to their right check area where the UVR imaging model algorithm 108 detects streaking and/or other physical characteristics of the product on the user's skin that indicate an inadequate amount of product application. As another example, the UVR imaging system 110 may apply the UVR imaging model algorithm 108 to the example image 130a, and the UVR imaging model algorithm 108 may determine that the user has incorrectly applied product to their forehead area where the UVR imaging model algorithm 108 detects inconsistent application (e.g., high variance of UVR absorption/remittance characteristics in a concentrated area) and/or other physical characteristics of the product on the user's skin that indicate an incorrect product application technique.

In various aspects, the UVR imaging model algorithm 108 is an artificial intelligence (AI) based model trained with at least one AI algorithm. Training of the UVR imaging model algorithm 108 involves image analysis of training images to configure weights of the UVR imaging model algorithm 108, used to predict and/or classify future images. For example, in various aspects herein, generation of the UVR imaging model algorithm 108 involves training the UVR imaging model algorithm 108 with a plurality of training images, where each of the training images contains pixel data depicting a respective UVA amount of UVA absorption or remittance as projected on a respective surface area and a respective UVB amount of UVB absorption or remittance as projected on the respective surface area. As previously mentioned, the respective surface area may be, for example, human skin, a flexible polymeric substrate (e.g., Bioskin), a rigid polymeric substrate (e.g., polymethyl methacrylate (PMMA) plates), other skin surfaces (e.g., pig skin surfaces, etc.), and/or any other suitable surface or combinations thereof. In some aspects, one or more processors of a server or a cloud-based computing platform (e.g., imaging server(s) 102) may receive the plurality of training images via a computer network (e.g., computer network 120). In such aspects, the server and/or the cloud-based computing platform may train the UVR imaging model algorithm 108 with the pixel data of the plurality of training images.

In various aspects, a machine learning imaging model, as described herein (e.g., UVR imaging model algorithm 108), may be trained using a supervised or unsupervised machine learning program or algorithm. The machine learning program or algorithm may employ a neural network, which may be a convolutional neural network, a deep learning neural network, or a combined learning module or program that learns in two or more features or feature datasets (e.g., pixel data) in particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. In some aspects, the artificial intelligence and/or machine learning based algorithms may be included as a library or package executed on imaging server(s) 102. For example, libraries may include the TENSORFLOW based library, the PYTORCH library, and/or the SCIKIT-LEARN Python library.

Machine learning may involve identifying and recognizing patterns in existing data (such as training a model based on pixel data within images having pixel data depicting a respective UVA amount of UVA absorption or remittance as projected on a respective surface area and a respective UVB amount of UVB absorption or remittance as projected on the respective surface area) in order to facilitate making predictions or identification for subsequent data (such as using the model on new pixel data of a new surface image in order to determine attributes of application of a product on the surface area depicted in the new surface image).

Machine learning model(s), such as the UVR imaging model algorithm 108 described herein for some aspects, may be created and trained based upon example data (e.g., "training data" and related pixel data) inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Surface image analysis may include training a machine learning based algorithm (e.g., the UVR imaging model algorithm 108) on pixel data of images of one or more example surfaces. Additionally, or alternatively, the surface image analysis may include using a machine learning imaging model, as previously trained, to determine, based on the pixel data (e.g., including their RGB values, monochromatic values, greyscale values, etc.) of the one or more images of the one or more example surfaces, attributes of application of a product on the surface area depicted in an image. The weights of the model may be trained via analysis of various RGB values of surface area pixels of one or more training images. For example, dark or low RGB values (e.g., a pixel with values R=25, G=28, B=31) resulting in dark or low monochromatic values may indicate a relatively high degree of product application on the surface area. A lighter RGB value (e.g., a pixel with R=181, G=170, and B=191) resulting in a lighter monochromatic value may indicate a relatively low degree of product application on the surface area. In this manner, pixel data (e.g., detailing one or more attributes of application of a product on a surface area) of 10,000s training images may be used to train or use a machine learning imaging algorithm to determine attributes of application of a product on the surface area depicted in an image.

Figure 4:
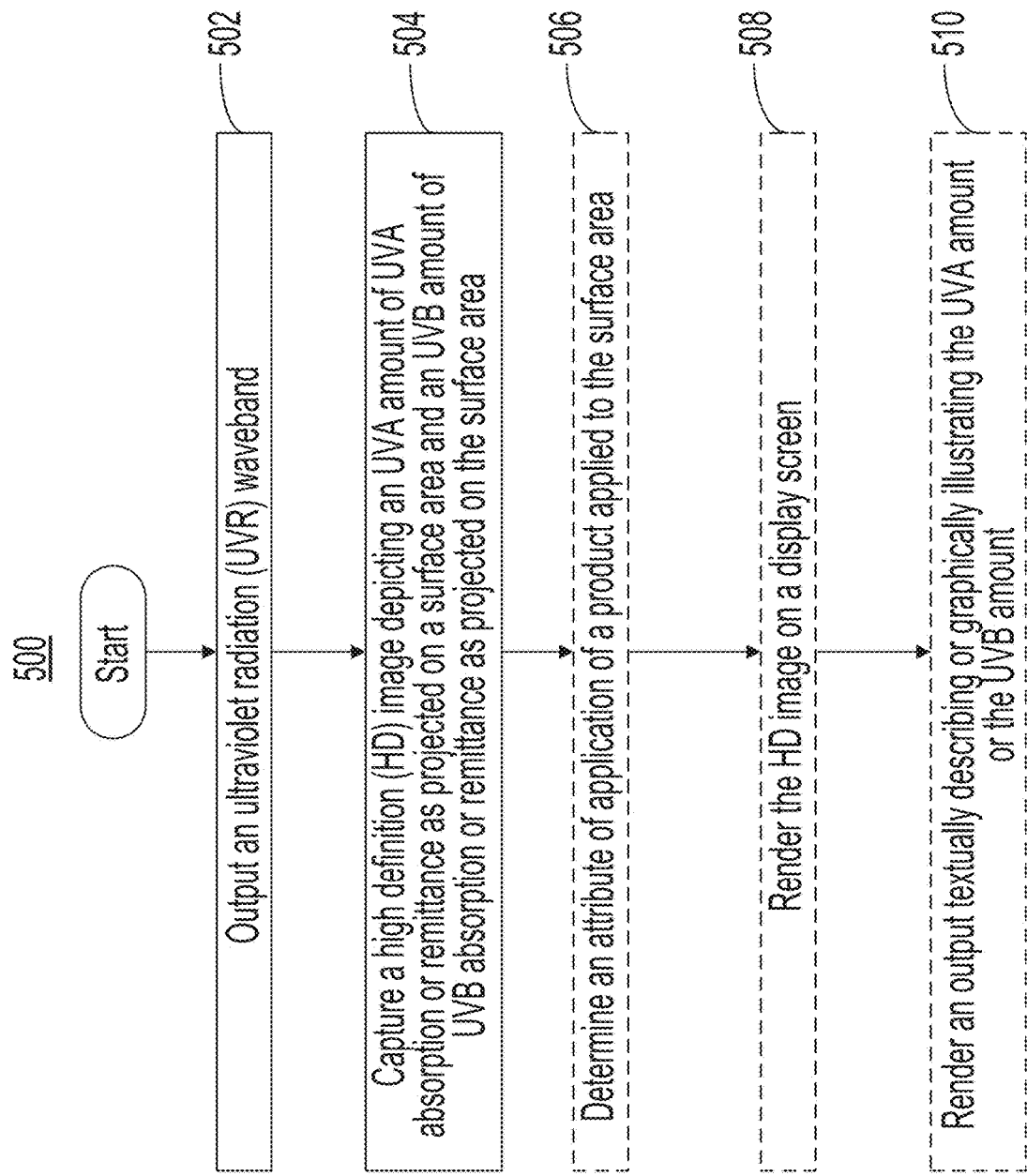
FIG. 4 is a diagram of an exemplary UVR imaging method.

FIG. 4 illustrates a diagram of a UVR imaging method 500 for capturing images (e.g., images 130*a*, 130*b*, and/or 130*c*) depicting absorption or remittance of UVR, for example, using one or more of the UVR imaging systems described herein. The images are generally pixel images as captured by a digital camera (e.g., camera 214). In some aspects, an image may include or refer to a plurality of images (e.g., frames) as collected using a digital video camera. Frames are consecutive images defining motion, such as in a movie, a video, or the like.

At block 502, the method 500 includes outputting an UVR waveband. For example, a suitable radiation source (e.g., radiation source 204, UVR light source 216) may output radiation in one or more UVR wavebands. The radiation source may be communicatively coupled with and/or integrated as part of a UVR imaging system, and the radiation source may output the one or more UVR wavebands in response to receiving a trigger from the UVR imaging system. The trigger may indicate, for example, that the UVR imaging system is going to capture an image utilizing the UVR wavebands output by the radiation source.

At block 504, the method 500 includes capturing, by a camera, an image depicting an UVA amount of UVA absorption or remittance as projected on a surface area (e.g., skin surface) and an UVB amount of UVB absorption or remittance as projected on the surface area. The UVR waveband may pass through a filter component (e.g., UVR bandpass filter 208) configured to differentiate at least one of a UVA waveband and a UVB waveband of the UVR waveband, and the UVR waveband may further pass through a polarizer component (e.g., UVR polarization filters 206*a*, 206*b*) configured to cross polarize each of the UVA waveband and the UVB waveband.

In some aspects, the image is captured during or after application of a product to the surface area. Further, the UVA amount and/or the UVB amount may be measured and/or recorded as part of the analysis of the image (e.g., via the UVR imaging model algorithm 108). For example, a user may apply sunscreen to a portion of the user's skin, and the user may thereafter utilize the UVR imaging system to capture an image(s) of the portion of the user's skin where the user applied the sunscreen. As another example, the user may apply a first amount of sunscreen to the portion of the user's skin, and may then capture an image(s) of the portion of the user's skin where the user applied the sunscreen. The user may then apply additional sunscreen to the portion of the user's skin, and then capture a subsequent image of the user's portion of skin to analyze differences in application amount/coverage, etc.

As yet another example, the user may utilize the present UVR imaging system to capture a video sequence of the user applying sunscreen to the user's skin. The UVR imaging system may capture the video sequence of the user applying sunscreen, and may measure the amount of product application on the user's skin during the video sequence (e.g., at each frame of the video sequence, every other frame of the video sequence, etc.). Further, in each of the above examples, the UVR imaging system may store/record the amount of product applied to the user's skin, and may also store the amount of product applied over time (e.g., during a video sequence, before/after images, etc.) in memory.

At optional block 506, the method 500 may include determining an attribute of application of a product applied to the surface area. Generally, the attribute of application may include one or more attributes of application, and the attribute(s) may include, for example, an amount of product applied to the surface area, an application quality of the product applied to the surface area, and/or any other suitable attribute(s) or combinations thereof. The UVR imaging system may determine the attribute of application using a rules-based analytical approach stored in local memory, by transmitting the image data to a remote processing platform (e.g., server(s) 102) for processing and receiving the determined attribute(s), and/or by applying a UVR imaging model algorithm (e.g., UVR imaging model algorithm 108) stored locally and/or remotely to the captured image.

The UVR imaging system may include an imaging model (e.g., UVR imaging model algorithm 108) trained with a plurality of images, each image depicting a respective UVA amount of UVA absorption or remittance as projected on a respective surface area and a respective UVB amount of UVB absorption or remittance as projected on the respective surface area. The imaging model may be stored on a non-transitory computer-readable medium of the UVR imaging system that includes computing instructions that are executable by one or more processors of the UVR imaging system. The computing instructions, when executed by the one or more processors, may cause the one or more processors to analyze, with the imaging model, the image to determine one or more attributes of application of the product. The one or more attributes may be, for example, predictions from the imaging model related to the homogeneity of application of the product to the surface area, an amount of streaking associated with the application of the product to the surface area, and/or any other suitable attribute(s) or combinations thereof. Further, the one or more attributes may be specific to a user's skin of a user depicted in the image.

The UVR imaging system may adjust the UVA amount or the UVB amount projected on the surface area by a diffuse reflectance standard. Generally, adjusting the UVA amount and/or the UVB amount includes adjusting the brightness of the image to account for the difference in absorption/remittance levels of UVA radiation and UVB radiation on a surface. The diffuse reflectance standard may be any suitable value such as from approximately 1% reflectance to approximately 20% reflectance based upon the surface represented in the image. For example, human skin may absorb more UVB radiation than UVA radiation due to the effects of melanin within the skin, and the diffuse reflectance standard may be approximately 10% reflectance (e.g., a Spectralon diffuse reflectance standard) to compensate for this effect.

At optional block 508, the method 500 may include rendering the image on a display screen that is visible to the user. Generally, the rendered image may display the UVA amount of UVA absorption or remittance as projected on the imaged surface area and/or the UVB amount of UVB absorption or remittance as projected on the imaged surface area. In some aspects, the surface area may be human skin (e.g., of a user), and the image may depict one or more product application patterns on the human skin. For example, the product may be sunscreen, and the one or more product application patterns may be indicative of protection from sunlight (e.g., UVR).

At optional block 510, the method 500 may include rendering an output textually describing or graphically illustrating the UVA amount or the UVB amount. Generally, the output may indicate an application effectiveness (e.g., application quality, application quantity, etc.) of the product to the surface area. In some aspects, the UVR imaging system may display the output on a display screen of a mobile device (e.g., mobile device 212) to inform the user of at least one of an application quality of a product to the user's skin, or an application quantity of the product to the user's skin. For example, the application quality may be an indication of the homogeneity of distribution of the product on the user's skin, and the UVR imaging system may further provide textual instructions/graphical indications to the user recommending application techniques to improve the homogeneity of distribution of the product on the user's skin. As another example, the application quantity may be an indication of the dose of product on the user's skin, and the UVR imaging system may further provide textual instructions/graphical indications to the user recommending an amount of product the user should apply/remove from the user's skin surface to optimally utilize the product.

The imaging model (e.g., UVR imaging model algorithm 108) may be trained to generate an output by analyzing the image of the application of the product to the surface. Computing instructions stored on the UVR imaging system, when executed by one or more processors, may cause the one or more processors to analyze, with the imaging model, the image to generate the output based on the attribute(s) of application of the product. For example, the output may be and/or include a determination of the effectiveness of a sunscreen product applied to a user's skin surface, and may indicate to a user whether or not the user has applied the sunscreen product to the user's skin surface in a manner (e.g., quantity, quality of application, etc.) that may effectively block UVR and/or a predicted length of time the user's application of the sunscreen product may effectively protect the user's skin surface from UVR. Further, in this example, the imaging model may determine the effectiveness of the sunscreen product by analyzing the pixel hue/darkness/intensity across a particular surface area unit of the user's skin surface to determine a specific dose of the sunscreen on the particular surface area unit. If the pixel hue/darkness/intensity does not satisfy a quantity threshold, the imaging model may determine that the user has not applied a sufficient amount of sunscreen on the particular surface area unit of the user's skin surface. Moreover, as discussed further herein, the UVR imaging system may include a display screen configured to receive the image and to render the image (optional block 508) and the output in real-time or near real-time upon or after capture of the image by the UVR imaging system.

The output may be a user-specific product recommendation for a manufactured product that may be designed to address an attribute of application determined by the UVR imaging system. For example, the output may recommend that the user apply a different/additional product to the surface area, such as a higher SPF sunscreen and/or a sunscreen that is configured to block a different waveband of UVR (e.g., UVB sunscreen v. UVA sunscreen).

Moreover, in some aspects, the UVR imaging system (e.g., via the UVR imaging model algorithm 108) may compare a first image to a second image to generate the output. For example, a user may initially capture a first image of a surface area (e.g., the users skin surface) including a first amount of sunscreen. After the user has applied more sunscreen, the user may capture a second image of the user's skin surface including a second amount of sunscreen, and the UVR imaging system may calculate a difference in application quality and/or application quantity by comparing the first amount in the first image to the second amount in the second image.

As another example, a user may apply sunscreen to a target skin surface at the beginning of a first day, and the user may capture a first image of the target skin surface using the UVR imaging system at the beginning of the first day. The user may then capture a second image of the target skin surface later in the first day, and the UVR imaging system may calculate/determine a wear effect of the sunscreen across the first day that indicates, for example, an amount of the sunscreen initially applied by the user that has worn off of skin surface throughout the first day. The UVR imaging system may additionally determine an effective protection factor (EPF) related to the wear effect that may indicate to the user at the beginning of the first day a length of time the amount of sunscreen applied to the user's skin surface may protect the user's skin surface from UVR. The UVR imaging system may also determine the EPF based upon a known activity level of the user. For example, athletic users may have a lower EPF for a comparable application of sunscreen than a sedentary user that remains indoors for long periods of time during the day. The EPF determined by the UVR imaging system may be communicated to the user, for example, on a display screen of a mobile device.

Figure 5:
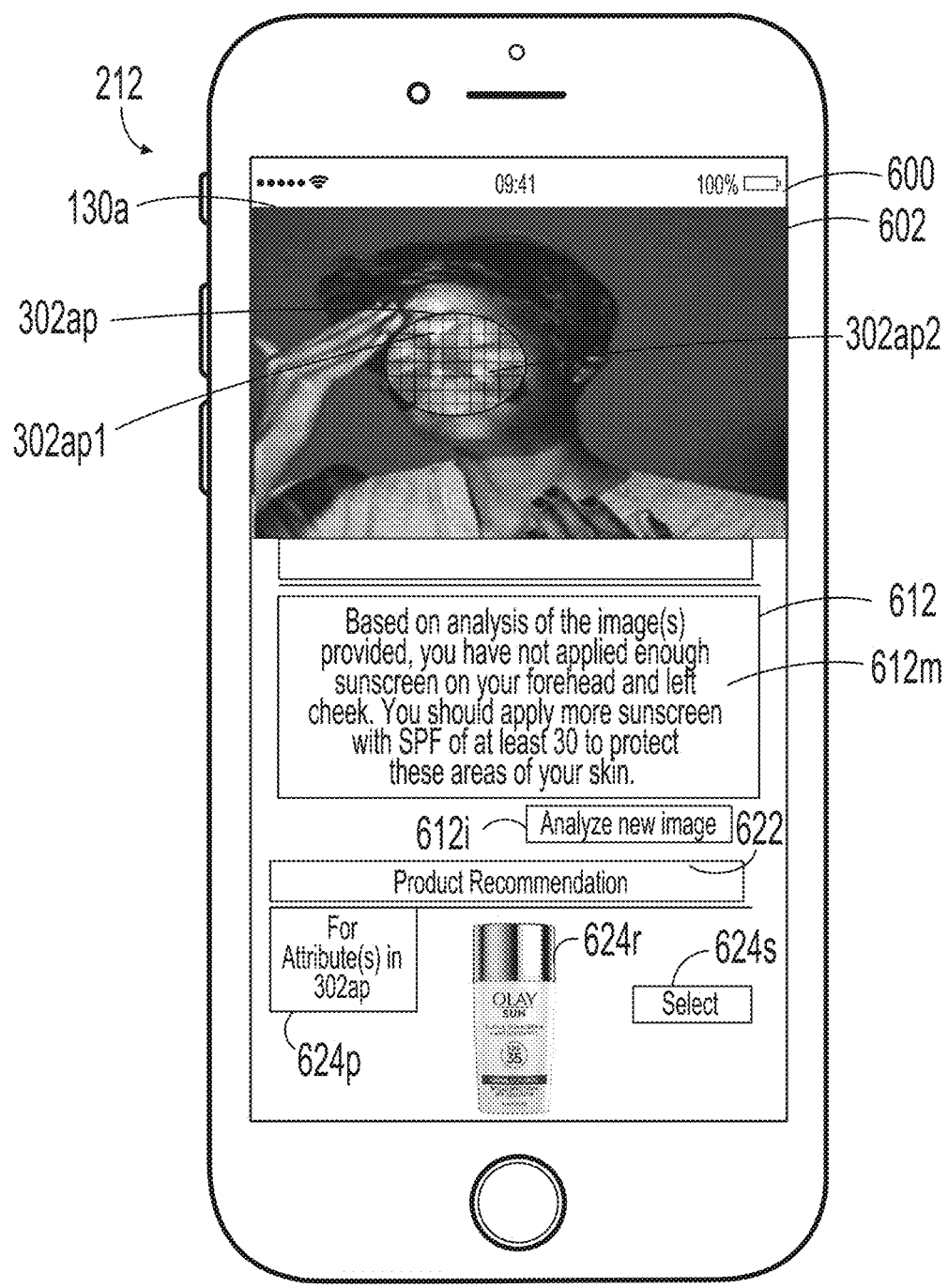
FIG. 5 illustrates an example user interface, as rendered on a display screen of a user computing device.

FIG. 5 illustrates an example of a graphical display that includes a user interface 602 rendered on a display screen 600 of a mobile device 212. The user interface 602 may be implemented or rendered via a native or web-based application (app) executing on the mobile device 212. Of course, the display screen 600 may be representative of a display screen on any suitable UVR imaging system (e.g., example UVR imaging systems 200a, 200b).

Figure 6:
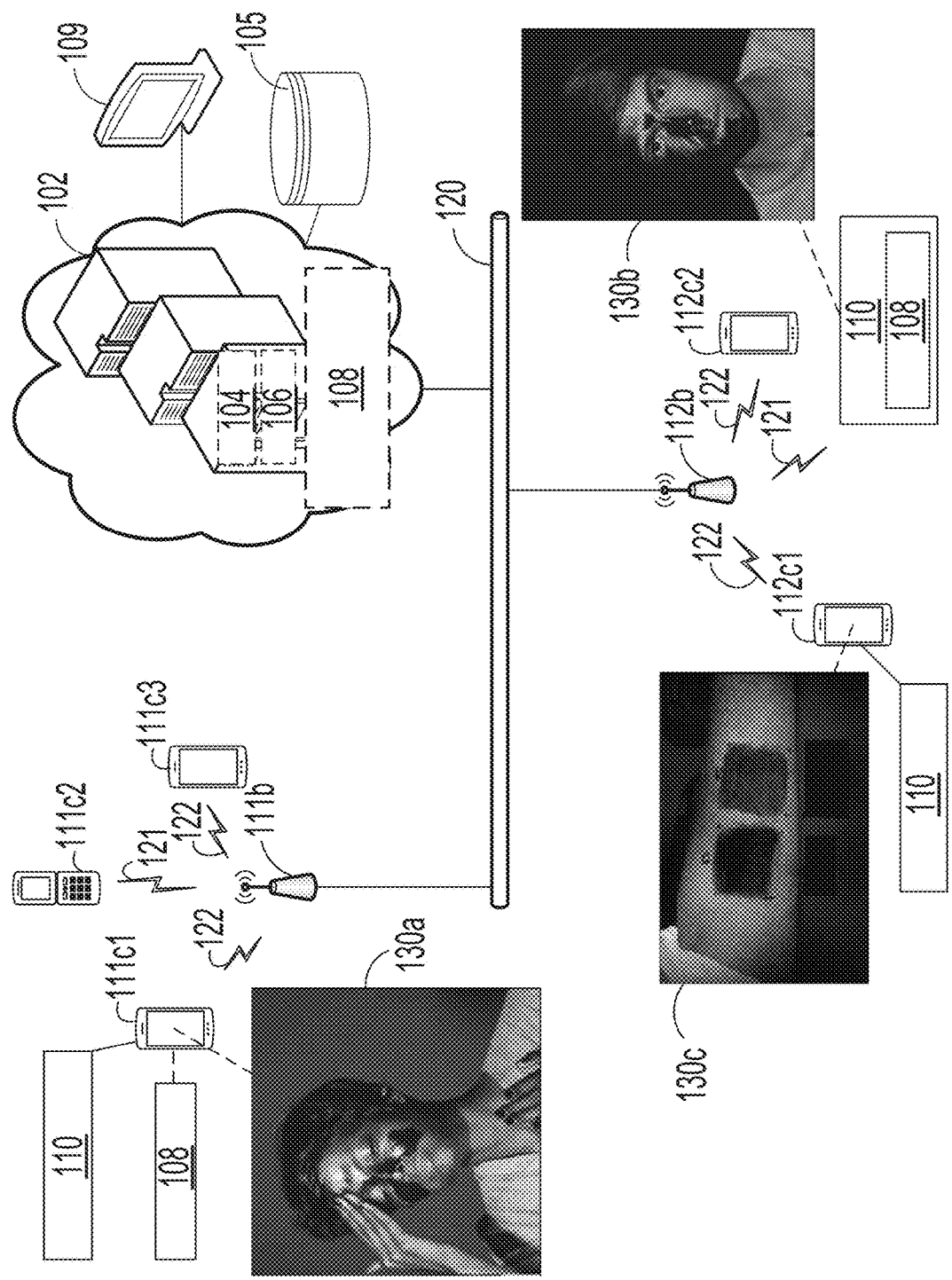
FIG. 6 illustrates an example ultraviolet radiation (UVR) imaging system environment.

As illustrated in FIG. 5, the mobile device 212 is a user computing device as described for FIGS. 1B and 6, e.g., where the user computing device 111c1 and the mobile device 212 are illustrated as APPLE iPhones that implement the APPLE iOS operating system, and the mobile device 212 has a display screen 600. The mobile device 212 may execute one or more native applications (apps) on its operating system. Such native apps may be implemented or coded (e.g., as computing instructions) in a computing language (e.g., SWIFT) executable by the user computing device operating system (e.g., APPLE iOS) by the processor of the mobile device 212. Additionally, or alternatively, the user interface 602 may be implemented or rendered via a web interface, such as via a web browser application, e.g., Safari and/or Google Chrome app(s), or other such web browser or the like.

As shown in the example of FIG. 5, the user interface 602 includes a graphical representation (e.g., example image 130a) of the user's skin. The graphical representation may be the example image 130a of the user's skin surface as captured by the UVR imaging system (e.g., example UVR imaging systems 200a, 200b), as described herein. In the example of FIG. 5, the example image 130a of the user's skin surface may be annotated with one or more graphics (e.g., area of pixel data 302ap), textual rendering, and/or any other suitable rendering or combinations thereof corresponding to the UVA amount of UVA absorption or remittance as projected on the example image 130a and the UVB amount of UVB absorption or remittance as projected on the example image 130a of the user's skin surface. It is to be understood that other graphical/textual rendering types or values are contemplated herein, where textual rendering types or values may be rendered, for example, as attribute(s) of application of a product on the indicated portion of skin (e.g., at pixels 302ap1 and 302ap2), or the like. Additionally or alternatively, color values may be used and/or overlaid on a graphical representation shown on the user interface 602 (e.g., example image 130a) to indicate attribute(s) of application of a product on the user's skin surface (e.g., heat-mapping detailing areas with insufficient product application technique/quantity).

Other graphical overlays may include, for example, a heat map, where a specific color scheme overlaid onto the example image 130a indicates a magnitude or a direction of product application that a user should follow to achieve optimal product application. The example image 130a may also include textual overlays configured to annotate the relative magnitudes and/or directions indicated by arrow(s) and/or other graphical overlay(s). For example, the example image 130a may include text such as "Apply More Product," "Use Circular Motions," etc. to describe the attribute(s) indicated by arrows and/or other graphical representations. Additionally or alternatively, the example image 130a may include a percentage scale or other numerical indicator to supplement the arrows and/or other graphical indicators. For example, the example image 130a may include product application attribute(s) values from 0% to 100%, where 0% represents the least optimal amount of product application for a particular skin surface portion and 100% represents the optimal amount of product application for a particular skin surface portion. Values can range across this map where a product application amount value of 67% represents one or more pixels detected within the example image 130a that has a higher product application amount value than a product application amount value of 10% as detected for one or more different pixels within the same example image 130a or a different example image (of the same or different user and/or portion of skin). Moreover, the percentage scale or other numerical indicators may be used internally when the UVR imaging system (e.g., via UVR imaging model algorithm 108) determines the size and/or direction of the graphical indicators, textual indicators, and/or other indicators or combinations thereof.

The area of pixel data 302ap may be annotated or overlaid on top of the example image 130a to highlight the area or attribute(s) identified within the pixel data (e.g., feature data and/or raw pixel data) by the UVR imaging model algorithm 108. In the example of FIG. 5, the attribute(s) identified within the area of pixel data 302ap may include predictions from the UVR imaging model algorithm 108 related to the homogeneity of application of the product to the surface area (e.g., at pixel 302ap1), an amount of streaking associated with the application of the product to the surface area (e.g., at pixel 302ap2), and/or any other suitable attribute(s) or combinations thereof shown in the area of pixel data 302ap. In various aspects, the pixels identified as specific attribute(s) within the pixel data 302ap (e.g., pixel 302ap1 and pixel 302ap2) may be highlighted or otherwise annotated when rendered.

User interface 602 may also include or render an output 612. In the aspect of FIG. 5, the output 612 is a user-specific recommendation that includes a message 612m to the user designed to address an attribute identifiable within the pixel data (e.g., pixel data 302ap) of the user's skin surface. As shown in the example of FIG. 5, the message 612m includes a product recommendation for the user to apply a sunscreen product to the user's forehead and left cheek, based on an analysis performed by the UVR imaging model algorithm 108 that indicated the user did not apply a sufficient amount of sunscreen to those areas to adequately protect the user's forehead and left cheek from harmful exposure to UVR. The product recommendation may be correlated to the identified attribute(s) within the pixel data (e.g., high SPF sunscreen to alleviate exposure to UVR), and the mobile device 212 may be instructed to output the product recommendation when the attribute (e.g., insufficient product application amount/technique, etc.) is identified.

The user interface 602 may also include or render a section for a product recommendation 622 for a manufactured product 624r (e.g., sunscreen, as described above). The product recommendation 622 generally corresponds to the output 612, as described above. For example, in the example of FIG. 5, the output 612 may be displayed on the display screen 600 of the mobile device 212 with instructions (e.g., message 612m) for addressing, with the manufactured product (manufactured product 624r (e.g., sunscreen))

attribute(s) of application (e.g., insufficient product application amount at pixels 302ap1, 302ap2) identifiable in the pixel data (e.g., pixel data 302ap) of the user's skin surface.

In the example of FIG. 5, the output or analysis of image(s) (e.g. example image 130a) using the UVR imaging model algorithm 108, may be used to generate or identify recommendations for corresponding product(s). Such recommendations may include products such as hydrating/moisturizing lotion, exfoliator, sunscreen, cleanser, shaving gel, or the like to address the attribute(s) detected within the pixel data by the UVR imaging model algorithm 108. In the example of FIG. 5, the user interface 602 renders or provides a recommended product (e.g., manufactured product 624r), as determined by the UVR imaging model algorithm 108, and its related image analysis of the example image 130a and its pixel data and various features. In the example of FIG. 5, this is indicated and annotated (624p) on the user interface 602.

The user interface 602 may further include a selectable UI button 624s to allow the user to select for purchase or shipment the corresponding product (e.g., manufactured product 624r). In some aspects, selection of the selectable UI button 624s may cause the recommended product(s) to be shipped to the user and/or may notify a third party that the user is interested in the product(s). For example, either the mobile device 212 and/or the imaging server(s) 102 may initiate, based on the output 612, the manufactured product 624r (e.g., sunscreen) for shipment to the user. In such aspects, the product may be packaged and shipped to the user.

In various aspects, the graphical representation (e.g., example image 130a), with graphical annotations (e.g., area of pixel data 302ap), and the output 612 may be transmitted, via the computer network (e.g., from an imaging server 102 and/or one or more processors) to the mobile device 212, for rendering on the display screen 600. In other aspects, no transmission to the imaging server(s) 102 of the user's specific image occurs, where the output (and/or product specific recommendation) may instead be generated locally, by the UVR imaging model algorithm 108 executing and/or implemented on a UVR imaging system (e.g., example UVR imaging systems 200a, 200b) and rendered, by a processor of the UVR imaging system, on the display screen 600 of the UVR imaging system (e.g., via mobile device 212).

In some aspects, as shown in the example of FIG. 5, the user may select selectable button 612i for reanalyzing (e.g., either locally at the UVR imaging system or remotely at imaging server(s) 102) a new image. Selectable button 612i may cause the user interface 602 to prompt the user to position the UVR imaging system over the user's skin surface to capture a new image and/or for the user to select a new image for upload. The UVR imaging system and/or the imaging server(s) 102 may receive the new image of the user before, during, and/or after performing some or all of the product application options/suggestions presented in the output 612. The new image (e.g., just like the example image 130a) may include pixel data of the user's skin surface. The UVR imaging model algorithm 108, executing on the memory of the UVR imaging system, may analyze the new image captured by the UVR imaging system to determine one or more attribute(s) of the user's skin surface depicted in the new image. The UVR imaging system may generate, based on the one or more attribute(s) of the user's skin surface depicted in the new image, a new output or comment regarding the one or more attribute(s) identifiable within the pixel data of the new image. For example, the new output may include a new graphical representation including graphics and/or text. The new output may include additional recommendations, e.g., that the user should apply the recommended product to the user's skin surface in a particular manner (e.g., using circular motions, etc.), that the user should apply the recommended product in a particular amount to the user's skin surface, or the like. A comment may also include that the user has corrected the attribute(s) identifiable within the pixel data (e.g., the user has a sufficient amount of sunscreen applied to the user's skin surface, the user has applied a sunscreen with more UVB absorption properties, etc.).

In some aspects, the new output or comment may be transmitted via the computer network to the UVR imaging system of the user for rendering on the display screen (e.g., display screen 600). In other aspects, no transmission to the imaging server(s) 102 of the user's new image occurs, where the new output (and/or product specific recommendation) may instead be generated locally, by the UVR imaging system (e.g., via UVR imaging model algorithm 108) and rendered, by a processor of the UVR imaging system, on a display screen (e.g., display screen 600) of the UVR imaging system.

FIG. 6 illustrates an example UVR imaging system environment 100 configured to facilitate analysis of pixel data of an image (e.g., image(s) 130a, 130b, and/or 130c) of a surface for depicting absorption or remittance of UVR, in accordance with various aspects disclosed herein. As referred to herein, a "surface" may refer to any portion of the human body including the torso, waist, face, head, arm, leg, or other appendage or portion or part of the user's body thereof, a flexible polymeric substrate (e.g., Bioskin), a rigid polymeric substrate (e.g., polymethyl methacrylate (PMMA) plates), other skin surfaces (e.g., pig skin surfaces, etc.), and/or any other suitable surface or combinations thereof. In the example aspect of FIG. 6, UVR imaging system environment 100 includes imaging server(s) 102 (also referenced herein as "server(s)"), which may include one or more computer servers. In various aspects imaging server(s) 102 include multiple servers, which may include a multiple, redundant, or replicated servers as part of a server farm. In still further aspects, imaging server(s) 102 may be implemented as cloud-based servers, such as a cloud-based computing platform. For example, server(s) 102 may be any one or more cloud-based platform(s) such as MICROSOFT AZURE, AMAZON AWS, or the like. Server(s) 102 may include one or more processor(s) 104 as well as one or more computer memories 106.

The memory 106 may include one or more forms of volatile and/or non-volatile, fixed and/or removable memory in electronic communication with one or more processors, such as read-only memory (ROM), electronic programmable read-only memory (EPROM), random access memory (RAM), erasable electronic programmable read-only memory (EEPROM), and/or other hard drives, flash memory, MicroSD cards, and others. The memory 106 may store an operating system (OS) (e.g., Microsoft Windows, Linux, Unix, etc.) capable of facilitating the functionalities, apps, methods, or other software as discussed herein. The memory 106 may also store an UVR imaging model algorithm 108, which may be an artificial intelligence based model, such as a machine learning model trained on various images (e.g., image(s) 130a, 130b, and/or 130c), as described herein. Additionally, or alternatively, the UVR imaging model algorithm 108 may also be stored in database 105, which is accessible or otherwise communicatively coupled to imaging server(s) 102, and/or in the memory of one or more user computing devices 111c1-111c3 and/or 112c1-112c3. The memory 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, an imaging based machine learning model or component, such as the UVR imaging model algorithm 108, where each may be configured to facilitate their various functionalities discussed herein. It should be appreciated that one or more other applications may be envisioned and that are executed by the processor(s) 104.

The processor(s) 104 may be connected to the memory 106 via a computer bus responsible for transmitting electronic data, data packets, or otherwise electronic signals to and from the processor(s) 104 and memory 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 104 (e.g., a relational database, such as Oracle, DB2, MySQL, or a NoSQL based database, such as MongoDB). The data stored in the memories 106 and/or the database 105 may include all or part of any of the data or information described herein, including, for example, training images and/or user images (e.g., either of which including any image(s) 130a, 130b, and/or 130c) or other information of the user, including demographic, age, race, skin type, or the like.

The imaging server(s) 102 may further include a communication component configured to communicate (e.g., send and receive) data via one or more external/network port(s) to one or more networks or local terminals, such as computer network 120 and/or terminal 109 (for rendering or visualizing) described herein. In some aspects, imaging server(s) 102 may include a client-server platform technology such as ASP.NET, Java J2EE, Ruby on Rails, Nodejs, a web service or online API, responsive for receiving and responding to electronic requests. The imaging server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some aspects, the imaging server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120. In some aspects, computer network 120 may include a private network or local area network (LAN). Additionally, or alternatively, computer network 120 may include a public network such as the Internet.

Imaging server(s) 102 may further include or implement an operator interface configured to present information to an administrator or operator and/or receive inputs from the administrator or operator. As shown in FIG. 6, an operator interface may provide a display screen (e.g., via terminal 109). Imaging server(s) 102 may also provide I/O components (e.g., ports, capacitive or resistive touch sensitive input panels, keys, buttons, lights, LEDs), which may be directly accessible via or attached to imaging server(s) 102 or may be indirectly accessible via or attached to terminal 109. According to some aspects, an administrator or operator may access the server 102 via terminal 109 to review information, make changes, input training data or images, and/or perform other functions.

As described above herein, in some aspects, imaging server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the model(s), such as AI models, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

As shown in FIG. 6, imaging server(s) 102 are communicatively connected, via computer network 120 to the one or more user computing devices 111c1-111c3 and/or 112c1-112c2 and a UVR imaging system 110 via base stations 111b and 112b. In some aspects, base stations 111b and 112b may include cellular base stations, such as cell towers, communicating to the one or more user computing devices 111c1-111c3 and 112c1-112c2 and the UVR imaging system 110 via wireless communications 121 based on any one or more of various mobile phone standards, including NMT, GSM, CDMA, UMMTS, LTE, 5G, or the like. Additionally or alternatively, base stations 111b and 112b may include routers, wireless switches, or other such wireless connection points communicating to the one or more user computing devices 111c1-111c3 and 112c1-112c2 and the UVR imaging system 110 via wireless communications 122 based on any one or more of various wireless standards, including by non-limiting example, IEEE 802.11a/b/c/g (WIFI), the BLUETOOTH standard, or the like.

Any of the one or more user computing devices 111c1-111c3 and 112c1-112c2 and the UVR imaging system 110 may include mobile devices and/or client devices for accessing and/or communications with imaging server(s) 102. In various aspects, the one or more user computing devices 111c1-111c3 and 112c1-112c2 and the UVR imaging system 110 may include a cellular phone, a mobile phone, a tablet device, a personal data assistance (PDA), or the like, including, by non-limiting example, an APPLE iPhone or iPad device or a GOOGLE ANDROID based mobile phone or tablet. In still further aspects, the one or more user computing devices 111c1-111c3 and 112c1-112c2 and the UVR imaging system 110 may include a home assistant device and/or personal assistant device, e.g., having display screens, including, by way of non-limiting example, any one or more of a GOOGLE HOME device, an AMAZON ALEXA device, an ECHO SHOW device, or the like.

Further, the one or more user computing devices 111c1-111c3 and 112c1-112c2 and the UVR imaging system 110 may include a retail computing device, configured in the same or similar manner, e.g., as described herein. The retail computing device(s) may include a processor and memory, for implementing, or communicating with (e.g., via server(s) 102), a UVR imaging model algorithm 108, as described herein. However, a retail computing device may be located, installed, or otherwise positioned within a retail environment to allow users and/or customers of the retail environment to utilize the UVR imaging systems and methods on site within the retail environment. For example, the retail computing device may be installed within a kiosk for access by a user. The user may then upload or transfer images (e.g., from a user mobile device) to the kiosk to implement the UVR imaging systems and methods described herein. Additionally or alternatively, the kiosk may be configured with a camera to allow the user to take new images (e.g., in a private manner where warranted) of himself or herself for upload and analysis. In such aspects, the user or consumer himself or herself would be able to use the retail computing device to receive and/or have rendered a depiction of an UVA amount of UVA absorption or remittance as projected on a surface area of the user's skin and an UVB amount of UVB absorption or remittance as projected on the surface area of the user's skin, as described herein, on a display screen of the retail computing device.

Additionally or alternatively, the retail computing device may be a mobile device (as described herein) as carried by an employee or other personnel of the retail environment for interacting with users or consumers on site. In such aspects, a user or consumer may be able to interact with an employee or otherwise personnel of the retail environment, via the retail computing device (e.g., by transferring images from a mobile device of the user to the retail computing device or by capturing new images by a camera of the retail computing device), to receive and/or have rendered a depiction of an UVA amount of UVA absorption or remittance as projected on a surface area of the user's skin and an UVB amount of UVB absorption or remittance as projected on the surface area of the user's skin, as described herein, on a display screen of the retail computing device.

In addition, the one or more user computing devices 111c1-111c3 and 112c1-112c2 and the UVR imaging system 110 may implement or execute an operating system (OS) or mobile platform such as Apple's iOS and/or Google's Android operation system. Any of the one or more user computing devices 111c1-111c3 and 112c1-112c2 and the UVR imaging system 110 may include one or more processors and/or one or more memories for storing, implementing, or executing computing instructions or code, e.g., a mobile application or a home or personal assistant application, configured to perform some or all of the functions of the present disclosure, as described in various aspects herein. As shown in FIG. 6, the UVR imaging model algorithm 108 may be stored locally on a memory of a user computing device (e.g., user computing device 111c1). Further, the mobile application stored on the user computing devices 111c1-111c3 and/or 112c1-112c2 may utilize the UVR imaging model algorithm 108 to perform some or all of the functions of the present disclosure. The UVR imaging system 110 may locally store the UVR imaging model algorithm 108, and may similarly perform some or all of the functions of the present disclosure.

In addition, the one or more user computing devices 111c1-111c3 and 112c1-112c2 and the UVR imaging system 110 may include a digital camera and/or digital video camera for capturing or taking digital images and/or frames (e.g., which can be image(s) 130a, 130b, and/or 130c). Each digital image may include pixel data for training or implementing model(s) (e.g., UVR imaging model algorithm 108), such as artificial intelligence (AI), machine learning models, and/or rule-based algorithms, as described herein. For example, a digital camera and/or digital video camera of, e.g., any of the one or more user computing devices 111c1-111c3 and 112c1-112c2 and the UVR imaging system 110 may be configured to take, capture, or otherwise generate digital images and, at least in some aspects, may store such images in a memory of a respective device. In some aspects, a user may also attach the UVR imaging system 110 to a user computing device 111c1-111c3 and/or 112c1-112c2 to facilitate capturing images sufficient for the user computing device 111c1-111c3 and/or 112c1-112c2 to locally process the captured images using the UVR imaging model algorithm 108.

Still further, each of the one or more user computing devices 111c1-111c3 and 112c1-112c2 and the UVR imaging system 110 may include a display screen for displaying graphics, images, text, product recommendations, data, pixels, features, and/or other such visualizations or information as described herein. These graphics, images, text, product recommendations, data, pixels, features, and/or other such visualizations or information may be generated, for example, by the respective device(s) as a result of implementing the UVR imaging model algorithm 108 utilizing images captured by a camera of the respective device(s) (e.g., the UVR imaging system 110 and/or a user computing device 111c1-111c3 and/or 112c1-112c2 utilizing the UVR imaging system 110). In various aspects, graphics, images, text, product recommendations, data, pixels, features, and/or other such visualizations or information may be received by server(s) 102 for display on the display screen of any one or more of the one or more user computing devices 111c1-111c3 and 112c1-112c2, the UVR imaging system 110, and/or the terminal 109. Additionally or alternatively, the one or more user computing devices 111c1-111c3 and 112c1-112c2 and the UVR imaging system 110 may include, implement, have access to, render, or otherwise expose, at least in part, an interface or a guided user interface (GUI) for displaying text and/or images on its display screen.

The one or more user computing devices 111c1-111c3 and 112c1-112c2 and the UVR imaging system 110 may include a wireless transceiver to receive and transmit wireless communications 121 and/or 122 to and from base stations 111b and/or 112b. Pixel based images (e.g., image(s) 130a, 130b, and/or 130c) may be transmitted via computer network 120 to imaging server(s) 102 for training of model(s) and/or imaging analysis as described herein.

Examples/Combinations

A. An ultraviolet radiation (UVR) imaging system configured to capture images depicting absorption or remittance of UVR, the UVR imaging system comprising: a camera comprising a monochrome camera sensor, the camera configured to capture images; a radiation source configured to output a UVR waveband; a filter component configured to differentiate at least one of a UVA waveband and a UVB waveband of the UVR waveband; and a polarizer component configured to cross polarize each of the UVA waveband and the UVB waveband, wherein the camera is configured to capture an image depicting an UVA amount of UVA absorption or remittance as projected on a surface area and an UVB amount of UVB absorption or remittance as projected on the surface area.

B. The system of paragraph A, wherein the surface area comprises an area of human skin.

C. The system of paragraph B, wherein the image depicts one or more product application patterns on the area of the human skin, the one or more product application patterns being indicative of protection from sunlight.

D. The system of any one of paragraphs A to C, wherein the UVA amount or the UVB amount is adjusted by a diffuse reflectance standard.

E. The system of any one of paragraphs A to D, wherein the radiation source has an output peak of between about 290 nm and 400 nm.

F. The system of any one of paragraphs A to E, wherein the filter component comprises a dichroic coated filter.

G. The system of any one of paragraphs A to F, wherein the filter component comprises a 313 nm narrow bandpass filter with a 10 nm full width half maximum and a 365 nm narrow bandpass filter with a 10 nm full width half maximum.

H. The system of any one of paragraphs A to G, wherein at least a portion of other radiation of the UVR waveband is filtered as depicted within the image.

I. The system of any one of paragraphs A to H, wherein the polarizer component polarizes electromagnetic radiation (EMR) of the UVR waveband having a wavelength of between 220 nm and 400 nm.

J. The system of any one of paragraphs A to I, wherein the polarizer component has a diameter of between about 10 mm and about 50 mm.

K. The system of any one of paragraphs A to J, wherein the radiation source has an output diameter to allow use of small diameter polarizers.

L. The system of any one of paragraphs A to K, wherein the radiation source is a continuous radiation source.

M. The system of any one of paragraphs A to L, wherein the radiation source is selected from at least one of: one or more xenon bulbs, one or more mercury xenon bulbs, or one or more light emitting diode (LED) sources.

N. The system of any one of paragraphs A to M, wherein the camera, the radiation source, the filter component, and the polarizer component comprise at least a portion of a UVR imaging device, the UVR imaging device configured for attachment to or integration with a mobile device.

O. The system of paragraph N, further comprising a mobile application (app) configured to operate on the mobile device and communicatively coupled to the UVR imaging device, wherein the mobile app comprises computing instructions executable by one or more processors of the mobile device, and stored on a non-transitory computer-readable medium of the mobile device, wherein the computing instructions, when executed by the one or more processors, cause the one or more processors to render, on a display screen of the mobile device, the image.

P. The system of paragraph O, wherein the computing instructions, when executed by the one or more processors, cause the one or more processors to render, on the display screen of the mobile device, an output textually describing or graphically illustrating the UVA amount or the UVB amount.

Q. The system of paragraph P, wherein the computing instructions, when executed by the one or more processors, cause the one or more processors to render, on the display screen of the mobile device, an output informing a user of at least one of an application quality of a product to the user's skin, or an application of a quantity of the product to the user's skin.

R. The system of any one of paragraphs A to Q, wherein the camera further comprises an apochromatic lens.

S. The system of any one of paragraphs A to R, further comprising: a processor; a memory communicatively coupled to the processor; an imaging model trained with a plurality of images each depicting a respective UVA amount of UVA absorption or remittance as projected on a respective surface area and a respective UVB amount of UVB absorption or remittance as projected on the respective surface area, the model trained to determine one or more respective attributes of application of a product; and computing instructions executable by the processor, and stored on the memory, wherein the computing instructions, when executed by the processor, cause the processor to: analyze, with the imaging model, the image to determine one or more attributes of application of the product, the one or more attributes specific to a user's skin as depicted in the image, wherein the surface area comprises skin.

T. The system of any one of paragraphs A to S, further comprising: a display screen configured to receive the image, wherein the display screen is configured to render the image in real-time or near real-time upon or after capture of the image by the camera.

U. The system of any one of paragraphs A to T, wherein the image is captured during or after application of a product to the surface area, and wherein the UVA amount or the UVB amount is measured or recorded.

V. A method of determining effectiveness of sunscreen on skin comprising: (a) applying sunscreen to skin; (b) determining the effectiveness of the sunscreen with the system of any one of paragraphs A to U.

W. A method of providing a message related to sunscreen use to a user, comprising: (a) applying sunscreen to skin; (b) determining a property of the sunscreen using the system of any one of paragraphs A to U; (c) communicating a message related to sunscreen use to a consumer based on the property in (b).

An ultraviolet radiation (UVR) imaging method for capturing images depicting absorption or remittance of UVR, the UVR imaging method comprising: outputting, by a radiation source, a UVR waveband; and capturing, by a camera, an image depicting an UVA amount of UVA absorption or remittance as projected on a surface area and an UVB amount of UVB absorption or remittance as projected on the surface area, wherein the camera comprises a monochrome camera sensor, the UVR waveband passes through a filter component configured to differentiate at least one of a UVA waveband and a UVB waveband of the UVR waveband, and the UVR waveband passes through a polarizer component configured to cross polarize each of the UVA waveband and the UVB waveband.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ranges are inclusive and combinable. The number of significant digits conveys neither a limitation on the indicated amounts nor on the accuracy of the measurements. All numerical amounts are understood to be modified by the word "about" unless otherwise specifically indicated. The systems and methods described herein can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An ultraviolet radiation (UVR) imaging system configured to capture images depicting absorption or remittance of UVR, the UVR imaging system comprising:
   a camera comprising a monochrome camera sensor;
   a radiation source configured to output a UVR waveband;
   a filter component configured to differentiate at least one of a UVA waveband and a UVB waveband of the UVR waveband; and
   a polarizer component configured to cross polarize each of the UVA waveband and the UVB waveband, wherein the polarizer component has a diameter of between about 10 mm and about 50 mm,
   wherein the camera is configured to capture an image depicting an UVA amount of UVA absorption or remittance as projected on a surface area and an UVB amount of UVB absorption or remittance as projected on the surface area.

2. The UVR imaging system of claim 1, wherein the surface area comprises an area of human skin.

3. The UVR imaging system of claim 2, wherein the image depicts one or more product application patterns on the area of the human skin, the one or more product application patterns indicative of protection from sunlight.

4. The UVR imaging system of claim 1, wherein the UVA amount or the UVB amount is adjusted by a diffuse reflectance standard.

5. The UVR imaging system of claim 1, wherein the radiation source has an output peak of between about 290 nm and 400 nm.

6. The UVR imaging system of claim 1, wherein the filter component comprises a dichroic coated filter.

7. The UVR imaging system of claim 1, wherein the filter component comprises a 313 nm narrow bandpass filter with a 10 nm full width half maximum and a 365 nm narrow bandpass filter with a 10 nm full width half maximum.

8. The UVR imaging system of claim 1, wherein at least a portion of other radiation of the UVR waveband is filtered as depicted within the image.

9. The UVR imaging system of claim 1, wherein the polarizer component polarizes electromagnetic radiation (EMR) of the UVR waveband having a wavelength of between 220 nm and 400 nm.

10. The UVR imaging system of claim 1, wherein the radiation source has an output diameter to allow use of small diameter polarizers.

11. The UVR imaging system of claim 1, wherein the radiation source is a continuous radiation source.

12. The UVR imaging system of claim 1, wherein the radiation source is selected from at least one of: one or more xenon bulbs, one or more mercury xenon bulbs, or one or more light emitting diode (LED) sources.

13. The UVR imaging system of claim 1, wherein the camera, the radiation source, the filter component, and the polarizer component comprise at least a portion of a UVR imaging device, the UVR imaging device configured for attachment to or integration with a mobile device.

14. The UVR imaging system of claim 13 further comprising a mobile application (app) configured to operate on the mobile device and communicatively coupled to the UVR imaging device, wherein the mobile app comprises computing instructions executable by one or more processors of the mobile device, and stored on a non-transitory computer-readable medium of the mobile device, wherein the computing instructions, when executed by the one or more processors, cause the one or more processors to render, on a display screen of the mobile device, the image.

15. The UVR imaging system of claim 14, wherein the computing instructions, when executed by the one or more processors, cause the one or more processors to render, on the display screen of the mobile device, an output textually describing or graphically illustrating the UVA amount or the UVB amount.

16. The UVR imaging system of claim 14, wherein the computing instructions, when executed by the one or more processors, cause the one or more processors to render, on the display screen of the mobile device, an output informing a user of at least one of an application quality of a product to the user's skin, or an application of a quantity of the product to the user's skin.

17. The UVR imaging system of claim 1, wherein the camera further comprises an apochromatic lens.

18. The UVR imaging system of claim 1 further comprising:
   a processor;
      a memory communicatively coupled to the processor;
      an imaging model trained with a plurality of images each depicting a respective UVA amount of UVA absorption or remittance as projected on a respective surface area and a respective UVB amount of UVB absorption or remittance as projected on the respective surface area, the model trained to determine one or more respective attributes of application of a product; and
      computing instructions executable by the processor, and stored on the memory, wherein the computing instructions, when executed by the processor, cause the processor to:
   analyze, with the imaging model, the image to determine one or more attributes of application of the product, the one or more attributes specific to a user's skin as depicted in the image, wherein the surface area comprises skin.

19. The UVR imaging system of claim 1 further comprising:
   a display screen configured to receive the image,
      wherein the display screen is configured to render the image in real-time or near real-time upon or after capture of the image by the camera.

20. The UVR imaging system of claim 1, wherein the image is captured during or after application of a product to the surface area, and wherein the UVA amount or the UVB amount is measured or recorded.

21. A method of determining effectiveness of sunscreen on skin comprising:
   (a) applying sunscreen to skin;
   (b) determining the effectiveness of the sunscreen with the system of claim 1.

22. A method of providing a message related to sunscreen use to a user, comprising:
   (a) applying sunscreen to skin;
   (b) determining a property of the sunscreen using the system of claim 1;
   (c) communicating a message related to sunscreen use to a consumer based on the property in (b).

* * * * *